(12) United States Patent
Kirakossian et al.

(10) Patent No.: US 7,179,660 B1
(45) Date of Patent: Feb. 20, 2007

(54) CARRIERS COATED WITH POLYSACCHARIDES, THEIR PREPARATION AND USE

(75) Inventors: Hrair Kirakossian, San Jose, CA (US); John S. Pease, Los Altos, CA (US); Carsten Schelp, Hockessin, DE (US); Marcel R. Pirio, San Jose, CA (US); Uwe Stöhr, Marburg-Molscht (DE); Andreas Wiegand, Schwalmstadt (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 10/220,623

(22) PCT Filed: Mar. 6, 2000

(86) PCT No.: PCT/US00/05978

§ 371 (c)(1),
(2), (4) Date: Apr. 14, 2003

(87) PCT Pub. No.: WO01/67105

PCT Pub. Date: Sep. 13, 2001

(51) Int. Cl.
*G01N 33/548* (2006.01)

(52) U.S. Cl. .................. 436/529; 435/6; 435/7.5; 435/969; 436/510; 436/532; 436/533; 436/534; 436/827; 428/403

(58) Field of Classification Search ............... None
See application file for complete search history.

(56) References Cited

U.S. PATENT DOCUMENTS

| | | | |
|---|---|---|---|
| 3,996,345 A | | 12/1976 | Ullman et al. |
| 5,169,754 A | * | 12/1992 | Siiman et al. .................. 435/5 |
| 5,427,767 A | * | 6/1995 | Kresse et al. ............... 424/9.32 |
| 5,466,609 A | * | 11/1995 | Siiman et al. ............... 436/518 |
| 5,527,684 A | | 6/1996 | Mabile et al. |
| 5,545,834 A | | 8/1996 | Singh et al. |
| 5,578,498 A | | 11/1996 | Singh et al. |
| 5,639,620 A | * | 6/1997 | Siiman et al. ............. 435/7.21 |
| 5,766,572 A | * | 6/1998 | Hasegawa et al. ....... 424/9.322 |

(Continued)

FOREIGN PATENT DOCUMENTS

EP    0 070 685 A2    1/1983

(Continued)

OTHER PUBLICATIONS

Ullman, et al.; *Proc. Natl. Acad. Sci.*; Luminescent Oxygen Channeling Immunoassay: Measurement of Particle Binding Kinetics by Chemiluminescense; 91; 5426-5430; 1994.

(Continued)

*Primary Examiner*—Christopher L. Chin
(74) *Attorney, Agent, or Firm*—Theodore J. Leitereg; Robert N. Carpenter

(57) ABSTRACT

A polysaccharide coated carrier having a coating of at least two successive layers of polysaccharide. The first polysaccharide layer spontaneously associates with a second polysaccharide layer and, optionally, the carrier. Each successive layer of polysaccharide spontaneously associates with a preceding layer. Spontaneous association occurs due to the presence of oppositely charged functional groups on each layer of polysaccharide or due to a spontaneous reaction between the functional groups the layers. The carrier may be any surface such as a tube, microtitration plate, bead, particle or the like and is suitable for use in diagnostic or therapeutic methods.

32 Claims, 7 Drawing Sheets

U.S. PATENT DOCUMENTS

| | | |
|---|---|---|
| 5,776,706 A | 7/1998 | Burshteyn et al. |
| 5,786,161 A | 7/1998 | Irsch et al. |
| 6,048,515 A * | 4/2000 | Kresse et al. ............ 424/9.322 |
| 6,576,221 B1 * | 6/2003 | Kresse et al. ............ 424/9.322 |

FOREIGN PATENT DOCUMENTS

| | | |
|---|---|---|
| EP | 0 275 139 A2 | 7/1988 |
| EP | 0 275 139 B1 | 4/1992 |
| EP | 0 515 194 A2 | 11/1992 |
| EP | 0 525 199 B1 | 5/1999 |
| WO | WO 84/03358 | 8/1984 |
| WO | WO 90/04178 | 4/1990 |
| WO | WO 94/09368 | 4/1994 |
| WO | WO 95/06877 | 3/1995 |
| WO | WO 96/04017 | 2/1996 |
| WO | WO 96/27394 | 9/1996 |
| WO | WO 99/30160 | 6/1999 |

OTHER PUBLICATIONS

Ullman, et al.; *Clin Chem*; Luminescent oxygen channeling assay (LOCI™): sensitive, broadly applicable homogeneous immunoassay method; 42:9; 1518-1626; 1996.

Bogulaski and Li; *Applied Biochemistry and Biotechnology*; Homogeneous Immunoassays; 7; 401-414; 1982.

Bystryak, et al.; *Anal. Bioche.*; A Homogeneous Immunofluorescence Assay Based on Dye-Sensitized Photobleaching; 225; 127-134; 1995.

Udenfriend, et al.; *Proc. Natl. Acad. Sci.*; Scintillation Proximity Radloimmunoassay Utilizing I-labeled Ligands; 82; 8672-8676; 1985.

Mathis, G.; *Clin. Chem.*; Rare Earth Cryptates and Homogeneous Fluoroimmumosassays with Human Sera; 39; 1953-1959; 1993.

Hart and Greenwald; *Molecular Immunology*; Scintillation Proximity Assay (SPA)-A New Method of Immunoassay; 16; 265-267; 1979.

* cited by examiner

Schematic Presentation for Double Coating
Labeling Chemisty for DexAl Bead

Schematic Presentation for Double Coating
Labeling Chemisty for COOH Bead

EFFECT OF THE ANTIBODY CONCENTRATION DURING THE LABELING REACTION IN DOUBLE COATING METHOD ON THE PERFORMANCE OF THE TSH LOCI ASSAY

CARRIERS COATED WITH POLYSACCHARIDES, THEIR PREPARATION AND USE

FIELD OF THE INVENTION

This invention relates to carriers having a surface coating of at least two layers of polysaccharides for use in the fields of medicine and clinical chemistry. These carriers are particularly useful in diagnostic and therapeutic methods. The invention relates further to methods for preparing the carriers.

BACKGROUND OF THE INVENTION

In the field of medicine and clinical chemistry, carriers such as magnetic or non-magnetic particles, beads, tubes, wells, microtitration plates, strips and sheets, are often used in vitro, e.g., in specific binding assays as a solid support and/or as a label, for affinity purification of substances, for separation of cells, or as enzyme carriers in enzymatic processes; or in vivo, e.g., as drug delivery systems, for the localization of disease sites or for measuring the blood flow in an organ. Usually, the carriers are associated with one or more specific binding pair partners.

Some of the difficulties associated with use of the carriers are (1) attaching specific binding partners to the carrier and, (2) preventing non-specific binding of undesired substances to the carrier from samples brought into contact with the carrier. Non-specific binding is the result of non-covalent binding between molecules that is relatively independent of specific surface structures. Non-specific binding may result from several factors including hydrophobic interactions between molecules.

The consequences of these problems include an unacceptably low number of specific binding partners associated to the carrier, poor performance of specific binding assays (high background and low sensitivity), and low purity in affinity purifications. Particular problems exist for carriers in the shape of particles which may agglutinate unspecifically and, in consequence, may form undesirable precipitates of aggregated particles.

Solutions to these problems have been approached through the use of carriers with hydrophilic polysaccharide coatings. In WO 90/04178 an immunoreactant carrier is described wherein a polysaccharide layer is coated to the surface of the carrier by covalent binding. The carrier described in WO 84/03358 is characterized by a surface which is only partially coated with a polysaccharide and elsewhere is not covered by such a coating but instead a specific binding partner is attached. The use of magnetic particles as pharmaceutical agents is described in WO 96/27394, wherein these particles are coated by alkali-treated polysaccharides. Iron-containing nanoparticles comprising of an iron-containing core and two polymer coatings are known from WO 96/04017. Squarate dyed carboxylate modified latex particles can be coated by maleimidated aminodextran according to EP 0 275 139.

Particles having multiple coating of aminodextrans are described in U.S. Pat. No. 5,639,620 and U.S. Pat. No. 5,707,877. Here, it is described that the multiple aminodextrans layers may be crosslinked through the use of a bifunctional crosslinking agents such as gluteraldehyde. The attachment of a biological substance to free amine groups on the outer layer of dextran also involves the use of the crosslinking agent. While this procedure allows for particles with multiple coatings of an amino dextran which should therefore diminish non-specific binding, the particles preparation and attachment to biological substances involve the use of the crosslinking reagent. This adds an extra step during the synthesis of the carrier or the attachment of biological substances. Further, the reactions involving the crosslinking reagent must be carefully controlled to avoid intra-layer and inter-particle crosslinking. Accordingly, it is still desirable to have a carrier where all of the surface is covered with a hydrophilic coating which is easily prepared and to which specific binding pair partners may be easily attached.

SUMMARY OF THE INVENTION

The present invention provides for a polysaccharide coated carrier comprising a carrier having a coating of at least two successive layers of polysaccharides. The first polysaccharide layer spontaneously associates with the second polysaccharide layer. Each successive layer of polysaccharide spontaneously associates with a preceding polysaccharide layer.

The polysaccharides have pendent functional groups and the functional groups of the successive polysaccharide layers are preferably charged oppositely of the functional groups of the preceding polysaccharide layers. The polysaccharide layers may be covalently coupled to each other by a reaction between the functional groups of the successive layers with a functional group of a preceding layer. This reaction may be a spontaneous reaction.

Preferably, the functional groups of the successive polysaccharide layers alternate between amine functional groups and amine reactive functional groups. The amine reactive functional groups may be an aldehyde or a carboxyl group.

A further embodiment of the invention is that the first polysaccharide layer spontaneously associates with the carrier. Both the carrier and the polysaccharide can have pendent functional groups, which preferably cause the spontaneous association. The functional groups of the carrier and the functional groups of the first polysaccharide layer may be oppositely charged or the functional groups of the carrier may spontaneously react with the functional groups of the first polysaccharide layer. The carrier may be covalently coupled to the polysaccharide layer by reaction between the functional groups of the carrier and the functional groups of the first polysaccharide layer. It is preferred that the functional groups of the carrier are amine reactive functional groups and the functional groups of the first polysaccharide layer are amine functional groups. The amine reactive functional group may be an aldehyde group or a carboxyl group.

In one aspect of the invention, the polysaccharide of the first coating layer is covalently coupled to said carrier by reaction between amine-reactive functional groups of the carrier and amine groups of the polysaccharide of the first coating layer. The polysaccharide of the second coating layer is covalently coupled to the first coating layer by reaction between the amine functional groups of the first coating layer and the amine-reactive functional groups of the polysaccharide of the second coating layer.

In another preferred embodiment of the present invention, the polysaccharide of the first coating layer is covalently coupled to said carrier by reaction between amine functional groups of the carrier and amine-reactive groups of the polysaccharide of the first coating layer. The polysaccharide of the second coating layer is covalently coupled to the first coating layer by reaction between the amine-reactive functional groups of the first coating layer and the amine functional groups of the polysaccharide of the second coating layer.

The use of at least two layers of polysaccharide, and particularly when the two polysaccharide molecules are different by their physico-chemical properties, results in better coverage of the carrier surface and minimizes unspecific binding. The oppositely charged functional groups on the carrier surface, e.g., $COO^-$-groups, and on the polysaccharide of the first coating layer, e.g., $N^+H_3$-groups, attract each other (spontaneously associate) and in the presence of excess polysaccharides the carrier surface is rapidly and effectively covered. Alternatively, the aldehyde groups —CO groups of an adelhyde derivatized polysaccharide molecule will spontaneously react with an amino group of an amine-derivatized carrier surface or polysaccharide. As excess amounts of polysaccharides can be used for the first and the other coating reactions, there is no need for fine monitoring of the polysaccharide concentration during the reactions. It has been found that the alternate coating of polysaccharide with amine functional groups and polysaccharide with amine-reactive functional groups is particularly advantageous with regard to a better coverage of the carrier and the simplicity of the coating procedure.

The reaction between the amine functional groups of the first coating layer and the amine-reactive functional groups of the polysaccharide of the second coating layer or alternatively the reaction between the amine-reactive functional groups of the first coating layer, and the amine functional groups of the polysaccharide of the second coating layer, leads also to an effective crosslinking of the polysaccharides and, in consequence, to a stable hydrophilic carrier coating. Furthermore, pendent amine-reactive functional groups of the second coating layer or outermost, respectively, can easily react with the amino groups of proteins or peptides. Coated particles prepared according to this invention demonstrates good colloidal stability over several months without observable precipitate in the storage tube.

One specific embodiment of the present invention is a carrier having a surface coating provided with a plurality of pendent functional groups, wherein (i) said surface coating comprises at least two alternately coated layers of polysaccharide with functional groups; (ii) the polysaccharide of the first coating layer is covalently coupled to said carrier by reaction between the functional groups of the carrier and the functional groups of the polysaccharide of the first coating layer; wherein the functional groups of the carrier and the functional groups of the polysaccharide of the first coating layer are oppositely charged; and (iii) the polysaccharide of the second coating layer is covalently coupled to the first coating layer by reaction between the functional groups of the first coating layer and the functional groups of the polysaccharide of the second coating layer, wherein the functional groups of the first coating layer and the functional groups of the polysaccharide of the second coating layer are oppositely charged.

A preferred carrier according to the present invention is a carrier having a surface coating provided with a plurality of pendent functional groups, wherein (i) said surface coating comprises at least two alternately coated layers of polysaccharide with amine functional groups and amine-reactive functional groups; (ii) the polysaccharide of the first coating layer is covalently coupled to said carrier by reaction between amine-reactive functional groups of the carrier and amine groups of the polysaccharide of the first coating layer; and (iii) the polysaccharide of the second coating layer is covalently coupled to the first coating layer by reaction between the amine functional groups of the first coating layer and the amine-reactive functional groups of the polysaccharide of the second coating layer.

Another preferred carrier according to the present invention is a carrier having a surface coating provided with a plurality of pendent functional groups, wherein (i) said surface coating comprises at least two alternately coated layers of polysaccharide with amine-reactive functional groups and amine functional groups; (ii) the polysaccharide of the first coating layer is covalently coupled to said carrier by reaction between amine functional groups of the carrier and amine-reactive groups of the polysaccharide of the first coating layer; and (iii) the polysaccharide of the second coating layer is covalently coupled to the first coating layer by reaction between the amine-reactive functional groups of the first coating layer and the amine functional groups of the polysaccharide of the second coating layer.

Still another preferred carrier according to the present invention is a carrier wherein said carrier material is selected from the group consisting of natural, synthetic or modified naturally occurring polymers such as agarose, cellulose, nitro-cellulose, cellulose acetate, polyvinylchloride, polystyrene, polyethylene, polypropylene, poly(4-methylbutene), polyacrylamide, polymethacrylate, polyethyleneterephthalate, nylon, polyvinylbutyrate or polyacrylat; silicones; glasses; ceramics; inorganic powders such as silica, magnesium sulfate and alumina; magnetic materials; metals or a combination thereof.

Another embodiment of the present invention is a carrier selected from the group consisting of tubes, microtitration plates, beads, particles and, preferably a magnetic or non-magnetic particle, most preferably a magnetic or non-magnetic carboxylated latex particle. If the carrier is a particle the preferred size range of 0.1 to 10 µm, preferably 0.1 to 5 µm, most preferably 0.15 to 3 µm. The carrier may be associated with substances such as a reporter molecule selected from the group consisting of dyes, radiolabels, sensitizers, fluorescers and/or chemiluminescers.

Another most preferred carrier according to this invention is a carrier wherein the polysaccharide of the second coating layer are dextrans wherein the amine-reactive functional groups are selected from the group consisting of aldehydes, carboxyl groups. Said dextrans have a preferred molecular weight of 10,000 to 2,000,000, preferably about 500,000.

Alternatively, the carrier according to the present invention can be a carrier wherein the polysaccharide of the first coating layer is a dextran with amine-reactive functional groups and, preferably, the polysaccharide of the second coating layer is an aminodextran.

Another embodiment of the present invention is a carrier wherein the pendent functional groups are selected from the group consisting of amines, aldehydes, carboxyl groups, maleimido groups, sulfhydryl groups and the like.

Still another embodiment of the present invention is a carrier wherein the pendent functional groups are used to bind specific binding partners to the surface coating of the carrier. Such a carrier is preferred wherein said specific binding partners are selected from the group consisting of antibodies, antibody fragments, receptors, oligonucleotides, oligonucleotide-binding proteins, lectins, haptens, antigens, immunoglobulin binding proteins, avidin, streptavidin and biotin.

Another embodiment of the present invention is a carrier according to this invention for use in in vitro and/or in vivo diagnostic methods, particularly in a method for the quantitative and/or qualitative determination of an analyte; and in therapeutic methods.

Still another embodiment of the present invention is a composition comprising a carrier according to this invention, preferably a particle, in a pharmaceutically acceptable medium.

Another embodiment of the present invention is a method for quantitative or qualitative determination of an analyte in a sample using a carrier according to this invention.

Still another embodiment of the present invention is a method for preparing a carrier according to this invention, said method comprising: (i) covalently coupling the polysaccharide of the first coating layer to said carrier by reaction between the amine-reactive functional groups of the carrier and the amine groups of the polysaccharide of the first coating layer; and (ii) covalently coupling the polysaccharide of the second coating layer to the first coating layer by reaction between the amine functional groups of the first coating layer and the amine-reactive functional groups of the polysaccharide of the second coating layer. A preferred method for preparing a carrier according to this invention is a method wherein carbodiimide conjugation chemistry is used for the coupling of the polysaccharide of the first coating layer to said carrier.

Another embodiment of the present invention is a method for preparing a carrier according to this invention, said method comprising: (i) covalently coupling the polysaccharide of the first coating layer to said carrier by reaction between the amine functional groups of the carrier and the amine-reactive groups of the polysaccharide of the first coating layer; and (ii) covalently coupling the polysaccharide of the second coating layer to the first coating layer by reaction between the amine-reactive functional groups of the first coating layer and the amine functional groups of the polysaccharide of the second coating layer. A preferred method for preparing a carrier according to this invention is a method wherein carbodiimide conjugation chemistry is used for the coupling of the polysaccharide of the first coating layer to said carrier.

Another preferred method for preparing a carrier according to this invention is a method wherein the coupling of the polysaccharide of the second coating layer to the first coating layer is done in the presence of a mild reducing agent, such as, e.g., sodium cyanoborhydride.

Still another preferred method for preparing a carrier according to this invention is a method wherein carbodiimide conjugation chemistry is used for the coupling of the polysaccharide of the second coating layer to the first coating layer.

One of the most preferred methods for preparing a carrier according to this invention is a method wherein the specific binding partners are covalently bound to the surface coating by reaction between the pendent functional groups of the surface coating and functional groups of the specific binding partners.

The preferred embodiments of the invention are described by claims 1 through 39.

DETAILED DESCRIPTION OF THE INVENTION

Figure 1A:
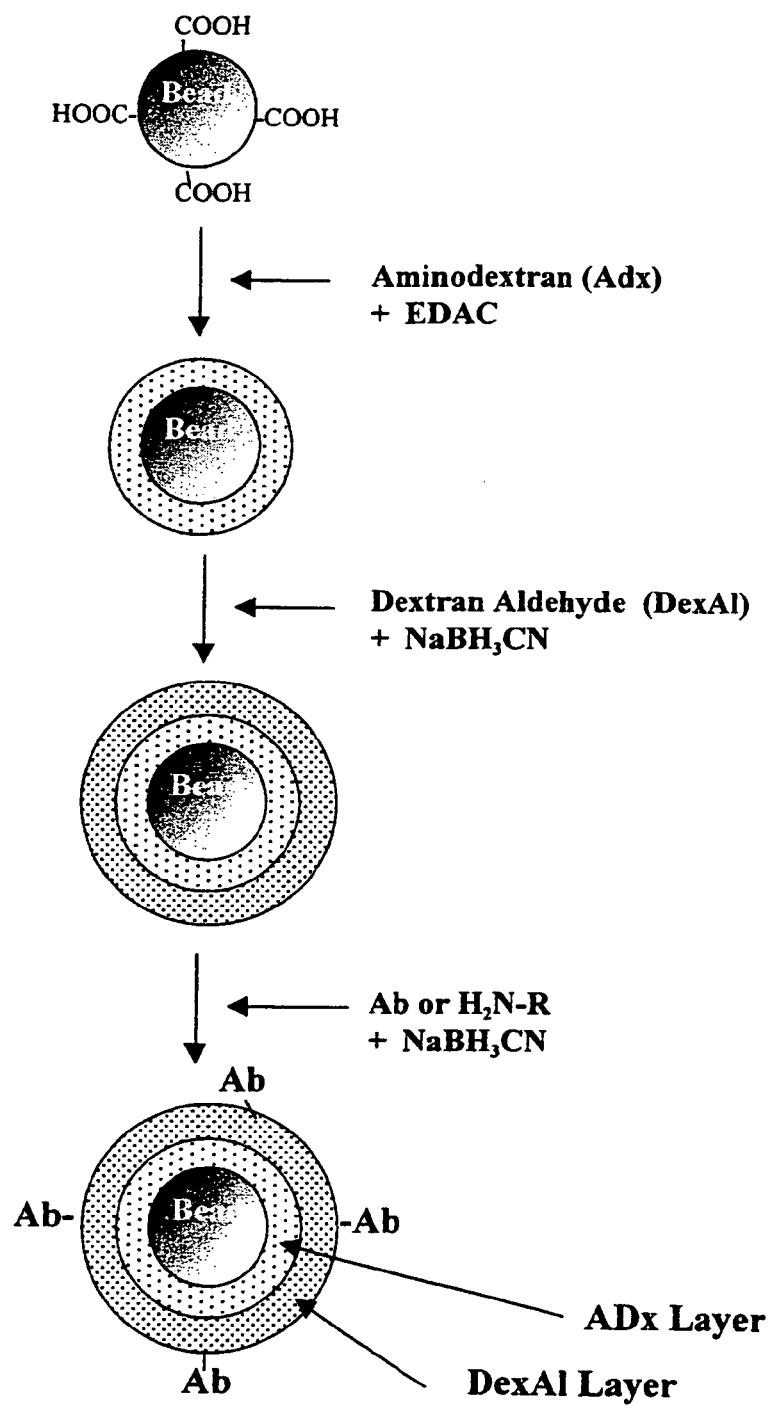
FIGS. 1A and 1B are schematic representations of two of the preferred embodiments for preparation of the carriers according to the present invention.

Before proceeding further with the description of specific embodiments of the present invention, a number of terms will be defined.

"Analyte", as used herein, means a compound or composition to be detected. The analyte can be a member of a specific binding pair and may be a monoepitopic (monovalent), usually haptenic, analyte and/or a polyvalent analyte, and is a single compound or plurality of compounds which share at least one common particular spatial and polar organization, e.g. an epitopic or determinant site. Possible analytes are also described in detail in U.S. Pat. No. 5,545,834, columns 3–10 (incorporated herein by reference)

The monoepitopic analytes will generally be from about 100 to 2,000 molecular weight, more usually from 125 to 1,000 molecular weight. The analytes include oligopeptides, oligonucleotides, drugs, metabolites, pesticides, pollutants, and the like. Representative analytes, by way of example and not limitation, include (i) alkaloids such as morphine alkaloids, which include morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites; (ii) steroids, which include the estrogens, androgens, andreocortical steroids, bile acids, cardiotonic glycosides and aglycones, which includes digoxin and digoxigenin, saponins and sapogenins, their derivatives and metabolites; steroid mimetic substances, such as diethylstilbestrol; (iii) lactams having from 5 to 6 annular members, which include the barbiturates, e.g., phenobarbital and secobarbital, diphenylhydantoin, primidone, ethosuximide, and their metabolites; (iv) aminoalkylbenzenes, with alkyl of from 2 to 3 carbon atoms, which include the amphetamines; catecholamines, which include ephedrine, L-dopa, epinephrine; narceine; papaverine; and metabolites of the above; (v) benzheterocyclics which include oxazepam, chlorpromazine, tegretol, their derivatives and metabolites, the heterocyclic rings being azepines, diazepines and phenothiazines; (vi) purines, which includes theophylline, caffeine, their metabolites and derivatives; (vii) drugs derived from marijuana, which include cannabinol and tetrahydrocannabinol; (viii) hormones such as thyroxine, cortisol, triiodothyronine, testosterone, estradiol, estrone, progesterone, and immunosuppressants such as cyclosporin, FK506, mycophenolic acid (MPA), and so forth; (ix) vitamins such as A, B, e.g. B12, C, D, E and K, folic acid, thiamine; (x) prostaglandins, which differ by the degree and sites of hydroxylation and unsaturation; (xi) tricyclic antidepressants, which include imipramine, dismethylimipramine, amitriptyline, nortriptyline, protriptyline, trimipramine, chlomipramine, doxepine, and desmethyldoxepin; (xii) anti-neoplastics, which include methotrexate; (xiii) antibiotics, which include penicillin, chloromycetin, actinomycetin, tetracycline, terramycin, the metabolites and derivatives; (xiv) nucleosides and nucleotides, which include ATP, NAD, FMN, adenosine, guanosine, thymidine, and cytidine with their appropriate sugar and phosphate substituentes; (xv) miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives; (xvi) metabolites related to diseased states include spermine, galactose, phenylpyruvic acid, and porphyrin Type 1; (xvii) aminoglycosides, such as gentamicin, kanamicin, tobramycin, and amikacin; and (xviii) pesticides such as polyhalogenated biphenyls, phosphate esters, thiophosphates, carbamates, polyhalogenated sulfenamides, their metabolites and derivatives.

Polyvalent analytes are normally poly(amino acids), i.e. polypeptides and proteins, polysaccharides, nucleic acids, and combinations thereof. Such combinations include components of bacteria, viruses, animal cells, plant cells and human cells, such as chromosomes, genes, mitochondria, nuclei, cell membranes and the like. For the most part, the polyepitopic ligand analytes will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, metabolism markers, tissue specific antigens, etc. Such proteins include, by way of illustration and not limitation, protamines; histones; albumins; globulins; scleroproteins; phosphoproteins; mucoproteins; chromoproteins; lipoproteins; nucleoproteins; glycoproteins; T-cell receptors; proteoglycans; HLA; proteins such as somatotropin, prolactin, insulin, pepsin; proteins found in human plasma; blood clotting factors; protein hormones such as, e.g., thyroid-stimulating hormone, follicle-stimulating hormone, luteinizing hormone, luteotropin, prolactin, chorionic gonadotropin; tissue hormones; cytokines; cancer antigens such as, e.g., PSA, CEA, a-fetoprotein, acid phosphatase, cytokeratins, neuron-specific enolase, CA19.9, CA 15-3 and CA125; tissue specific antigens such as, e.g., alkaline phosphatase, myoglobin, CPK-MB and calcitonin; and peptide hormones. Other polyvalent analytes of interest are mucopolysaccharides, polysaccharides and natural receptors including such materials as avidin, streptavidin, thyroxine binding globulin, thyroxine binding prealbumin, transcortin, etc.

The term analyte further includes oligonucleotide and polynucleotide analytes such as m-RNA, r-RNA, t-RNA, DNA (double stranded ("ds") or single stranded ("ss")), RNA (ds or ss), DNA-RNA duplexes, etc. An "oligonucleotide", as used herein, means usually a single stranded polynucleotide including a synthetic polynucleotide. The oligonucleotide(s) are usually comprised of a sequence of 10 to 100 nucleotides, preferably, 20 to 80 nucleotides in length. "Polynucleotide", as used herein, means usually a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. Polynucleotide includes nucleic acids from any source in purified or unpurified form, naturally occurring or synthetically produced, including DNA (dsDNA and ssDNA) and RNA (dsRNA and ssRNA), usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

The analyte may be a molecule found directly in a sample such as biological tissue, including excised tissue from an organ or other body part of a host, such as, e.g., a human or an animal, and body fluids, for example, urine, whole blood, plasma, serum, saliva, semen, stool, sputum, cerebral spinal fluid, tears, mucus, and the like. Preferably, the sample is urine, plasma or serum. The sample can be examined directly or may be pretreated to render the analyte more readily detectable by removing unwanted materials. The sample may be pretreated to separate or lyse cells; precipitate, hydrolyse or denature proteins; hydrolyze lipids; solubilize the analyte; or the like. Such pretreatment may include, without limitation: centrifugation; treatment of the sample with an organic solvent, for example, an alcohol, such as methanol; and treatment with detergents. The sample can be prepared in any convenient medium, which does not interfere with an assay. An aqueous medium is preferred.

The analyte may be amplified. An amplification of nucleic acids means any method that results in the formation of one or more copies of a nucleic acid. Numerous methods are known including the polymerase chain reaction (PCR), ligase chain reaction (LCR), amplification using Q beta replicase, nucleic acid sequence based amplification (NASBA), single primer amplification (ASPP) and others.

The analyte may be also a molecule found in food, water or in the environment, especially if the presence of said analyte gives evidence for a pollution or contamination of said food, water or environment.

The analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay.

"Analyte analog", as used herein, means a modified analyte, an analyte surrogate, or a modified analyte surrogate, all three referring to a compound having the capability of specifically binding a specific binding partner complementary to the analyte. The analyte surrogate is a different molecule than the analyte, but binds specifically to the specific binding partner complementary to the analyte. A modified analyte and a modified analyte surrogate differ from the analyte or the analyte surrogate, e.g., by being bound to a component of a signal producing system and/or to a solid support.

"Sample", as used herein, means the material suspected of containing the analyte. Such samples, preferably from humans or animals, include biological fluids such as blood, serum, plasma, sputum, lymphatic fluid, semen, vaginal mucus, feces, urine, spinal fluid, and the like; biological tissue such as hair, skin, sections or excised tissues from organs or other body parts; and so forth. Other samples include cell cultures and the like, plants, food, forensic samples such as paper, fabrics and scrapings, water, sewage, medicinals, etc. When necessary, the sample may be pretreated with reagents to liquefy the sample and release the analyte from binding substances.

"Specific binding pair", as used herein, means a pair of specific binding partners.

"Specific binding partner" or, in other words, "member of a specific binding pair", as used herein, means one of two molecules, usually different molecules, having an area on the surface or in a cavity which specifically binds to and is thereby defined as complementary with a particular spatial and polar organization of the other molecule. "Molecule", as used herein, can also mean a molecule complex such as an enzyme comprised of apoenzyme and coenzyme, an enzyme or a cellular receptor comprised of various subunits or a lipoprotein comprised of proteins and lipids. Illustrative specific binding partners include naturally occurring and synthetic molecules, e.g., thyroxine binding globulin, steroid-binding proteins, antibodies, Fab fragments or other antigen-binding fragments of antibodies, enzymes, lectins, nucleic acids, repressors, oligonucleotides, protein A, protein G, avidin, streptavidin, biotin, complement component C1q, or DNA binding proteins, RNA binding proteins and the like. The specific binding partners may be members of an immunological pair such as antigen-antibody or hapten-antibody, or may be operator-repressor, nuclease-nucleotide, biotin-avidin, lectin-polysaccharide, steroid—steroid binding protein, drug—drug-receptor, hormone—hormone receptor, enzyme-substrate, IgG-protein A, oligo- or polynucleotide-complementary oligo- or polynucleotide, and the like.

"Oppositely charged functional groups" means that the one group of functional groups are positively charged and the other negatively. The charge may depend on the selected reaction conditions, e.g. by the pH of the reaction medium. Reaction medium is a solution, usually a buffer, wherein the coupling reaction between the functional groups is performed.

"Antibody", as used herein, means an immunoglobulin which specifically binds to and is thereby defined as complementary with a particular spatial and polar organization of another molecule, usually called an antigen or a hapten. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

"A method for the quantitative and/or qualitative determination of an analyte", as used herein, means an assay for determining the presence or amount of an analyte. Quantitative, semiquantitative, and qualitative methods as well as all other methods for determining an analyte are considered to be methods of measuring the amount of an analyte. For example, a method which merely detects the presence or absence of an analyte in a sample suspected of containing the analyte is considered to be included within the scope of the present invention. The terms "detecting" and "determining," as well as other common synonyms for measuring, are contemplated within the scope of the present invention.

In the most common assays for the quantitative and/or qualitative determination of an analyte, the analyte is bound by a specific binding partner, preferably by a specific binding partner associated with a solid support and/or a component of a signal producing system, such as a label or a reporter molecule. Said specific binding partner may be bound directly, e.g. covalently or by adsorption, or indirectly to the solid support and/or to the component of a signal producing system. Indirect binding refers to the spatial association of two specific binding partners which are not members of a specific binding pair through a series of bonds between different binding pairs. Exemplary of indirect binding is the indirect binding of a biotinylated antibody to a label upon the binding of said biotinylated antibody to avidin attached to the label. A further example is the indirect binding of IgM to a solid support upon the binding of IgM to anti-IgM-antibodies attached to the solid support.

"Carrier", as used herein, means a solid phase, typically a support or surface, usually of an organic or inorganic, swellable or non-swellable, porous or non-porous, magnetic or non-magnetic, water-insoluble material that can have any one of a number of shapes, such as strip, sheet, rod, plate, well, tube, particle or bead. The surface can be hydrophilic or capable of being rendered hydrophilic. The solid support includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, polyvinylchloride, polyacrylamide, crosslinked dextran, agarose, polyacrylate, polyethylene, polypropylene, poly(4-methylbutene), polystyrene, polymethacrylate, polyethyleneterephthalate, nylon, polyvinylbutyrate, etc.; either used by themselves or in conjunction with other materials; glass available as Bioglass, ceramics, magnetic materials, metals, and the like. Natural or synthetic assemblies such as liposomes, phospholipid vesicles, and cells can also be employed.

A preferred carrier according to the present invention is selected from the group consisting of tubes, microtitration plates, wells, beads, magnetic and non-magnetic particles, filter papers, chromatographic papers. The most preferred carriers according to the present invention are magnetic or non-magnetic particles.

A carrier according to the present invention can be associated with reporter molecules such as dyes, radiolabels, sensitizers, fluorescers and/or chemiluminescers. The association of such substance(s) with particles utilized in the present invention, particularly with latex particles, may involve incorporation during formation of the particles by polymerization but will usually involve incorporation into preformed particles, usually by non-covalent dissolution into the particles. Usually a solution of the substance(s) will be employed. Solvents that may be utilized include alcohols, such as, e.g., ethanol, ethylene glycol and benzyl alcohol; amides such as, e.g., dimethyl formamide, formamide, acetamide and tetramethyl urea and the like; and ethers such as, e.g., carbitol, ethyl carbitol, dimethoxy ethane and the like; and water. The use of solvents having high boiling points in which the particles are insoluble permits the use of elevated temperatures to facilitate dissolution of the substance(s) into the particles and are particularly suitable. The solvents may be used singly or in combination. The solvents are preferred which do not interfere with signal-generating properties of the substance(s). The substances may also be covalently or non-covalently (e.g. by adsorption) bound to the carrier.

By way of illustration and not limitation, the preparation of particles associated with a sensitizer (chlorophyll) or with a chemiluminescer/fluorescer composition (dioxene, Eu(TTA)$_3$/TOPO) is described in U.S. Pat. No. 5,578,498, columns 31 and 32.

The coated carrier according to the present invention has pendent functional groups such as, e.g., maleimido groups, carboxyl groups, aldehydes, ketones, amino groups, sulfhydryl groups cyano groups, ethylene groups, hydroxyl groups, thiols, carboxamides, carbamates, carboxylic acid esters, sulfonic acids, sulfonic acid esters, phosphoric acids, phosphoric acid esters, ureas, phosphoramides, sulfonamides, ethers, sulfides, thioethers, olefins, acetylenes, amines, nitriles, halides and the like. These pendent functional groups can be used to bind specific binding partners to the surface coating of the carrier. Specific binding partners may include, for example, antibodies, antibody fragments, receptors, oligonucleotides, nucleotide-binding proteins, lectins, haptens, antigens, immunoglobulin binding proteins, avidin, streptavidin, biotin or other biological molecules.

"Particle" as used herein, means particles of at least 20 nm and not more than about 20 μm, usually at least about 40 nm and less than 10 μm, normally 0.1 to 10 g/m, preferably, 0.1 to 5 μm, most preferably 0.15 to 3 μm. "Particle", as used herein, encompasses spheres, spheroids, beads and other shapes as well. The particle may be organic or inorganic, swellable or non-swellable, porous or non-porous, having any density, but preferably of a density approximating water, generally from about 0.7 to about 1.5 g/ml, preferably suspendible in water, and composed of material that can be transparent, partially transparent, or opaque. The particles may be core-and-shell particles, such as particles with a magnetic core and a hard shell coating of polymerized monomer(s). The particles are preferably negative charged. The particles are preferably solid, e.g., polymer particles, metal sols (particles comprised of a heavy metal such as, e.g., gold or silver), glass particles, silicon particles, magnetic particles, dye crystallites. Most preferred a latex particles. "Latex", as used herein, means a particulate water-suspendible water-insoluble polymeric material. The latex is frequently a substituted polyethylene such as: polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyrridine, vinyl-chloride acrylate copolymers, and the like. Non-crosslinked polymers of styrene and carboxylated styrene or styrene functionalized with other active groups such as amino, hydroxyl, halo and the like are preferred. Frequently, copolymers of substituted styrenes with dienes such as butadiene will be used.

"Signal producing system", as used herein, means one or more components, at least one component being a detectable label, which generate a detectable signal that relates to the amount of bound and/or unbound label, i.e. the amount of label bound or not bound to the compound being detected. The label is any molecule that produces or can be induced to produce a signal, and may be, for example, a fluorescent compound (fluorescer), a radiolabel, an enzyme, a chemiluminescent compound (chemiluminescer) or a sensitizer. This molecule may be referred to as a "reporter molecule". Thus, the signal is detected and/or measured by detecting enzyme activity, luminescence, light absorbance, light scattering or radioactivity as the case may be.

Suitable labels include, by way of illustration and not limitation, enzymes such as alkaline phosphatase, glucose-6-phosphate dehydrogenase and horseradish peroxidase; dyes; fluorescers, such as fluorescein, rhodamine compounds, phycoerythrin, phycocyanin, allophycocyanin, o-phthaldehyde, fluorescent rare earth chelates, and fluorescamine; chemiluminescers such as isoluminol, and acridinium compounds; sensitizers, such as eosine, 9,10-dibromoanthracene, methylene blue, hematoporphyrin, phthalocyanines, chlorophyll, rose bengal; coenzymes; enzyme substrates; radiolabels such as $^{125}$I, $^{131}$I, $^{14}$C, $^{3}$H, $^{57}$Co and $^{75}$Se; particles, such as latex particles which may be further labeled with a reporter molecule or group of molecules such as a dye, sensitizer, fluorescer, chemiluminescers or other detectable molecule or group of molecules; metal sol; crystallite; liposomes and cells, which may be further labeled, etc.

There are numerous methods by which the label can produce a signal detectable by external means, desirably by visual examination, for example, by electromagnetic radiation, heat, and chemical reagents. The label or other signal producing system members can also be bound to a specific binding partner, another molecule or to a solid support.

Labels include groups detectable by means of electromagnetic radiation or by electrochemical detection including dyes, fluorescers, chemiluminescers, and radioactive isotopes.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal, which may include substrates, coenzymes, quenchers, enhancers, additional enzymes, substances that react with enzymatic products, catalysts, activators, cofactors, inhibitors, scavengers, metal ions, and a specific binding substance required for binding of signal generating substances.

The label and/or other signal producing system members may be bound to a specific binding partner or to a carrier according to the present invention. The label can be bound covalently to specific binding partner such as, for example, an antibody, biotin, avidin, an analyte analogue, an oligonucleotide or a hapten. Bonding of the label to the specific binding partner may be accomplished by chemical reactions that result in replacing a hydrogen atom of the label with a bond to the specific binding partner or may include a linking group between the label and the specific binding partner. Other signal producing system members may also be bound covalently to specific binding partners. For example, two signal producing system members such as a fluorescer and quencher can each be bound to a different antibody that forms a specific complex with the analyte. Formation of the complex brings the fluorescer and quencher in close proximity, thus permitting the quencher to interact with the fluorescer to produce a signal.

"Linking group", as used herein, means the covalent linkage between molecules. The linking group will vary depending upon nature of the molecules to be linked. Functional groups, such as thiol groups, amino groups, carboxyl groups, hydroxyl groups, phosphate groups or sulfo groups, that are normally present or are introduced on the molecule to be linked will be employed for linking. For example, two molecules functionalized with thiol groups may be conjugated by linking the thiols with a homobifunctional reagent, such as a bis-maleimide or a biyhaloacetyl compound. Two molecules functionalized with amine groups can be conjugated by use of homofunctional reagents such as glutaraldehyde or disuccinimidyl esters. Better control of a conjugation process may often be attained by utilizing a heterobifunctional reagent. For example, a molecule functionalized with thiol groups can be conjugated to a molecule functionalized with amine groups by means of a heterobifunctional reagent that possesses both maleimide and succinimidyl ester functions. Examples of heterobifunctional linkers include succinimidyl 4-(N-maleimidomethyl) cyclohexane-1-carboxylate (SMCC), succinimidyl 4-(iodoacetyl)aminobenzoate (SIAB) and succinimidyl 4-(p maleimidophenyl)butyrate.

"Carbodiimide conjugation chemistry", as used herein, means that chemical conjugates can be synthesized via available —COOH and —$NH_2$ groups to form an amide bond. This is ideal for preparing antibody or antigen conjugates. A first step in this synthesis is the conversion of carboxyl groups on one of the molecules to be conjugated to so-called active esters. The active esters can then react spontaneously with other functional groups, typically amines, on the other molecule to be conjugated. Most commonly carbodiimides, such as 1-Ethyl-3-[3-dimethylaminopropyl]-carbodiimide (EDC or EDAC) or 1-cyclohexyl-3-(2-morpholinyl-4-ethyl) carbodiimide (CMC) are used to convert carboxyl groups to active esters.

"Assay" means determining the presence or amount of an analyte in a sample suspected of containing an analyte, which is combined in an assay medium with reagents for carrying out the assay. Such reagents can include specific binding partners for the analyte, analyte analogs, solid surfaces to which one of the above reagents is bound, specific binding partners for the specific binding partners for the analyte. One or more of the reagents can be labelled. The reagents are chosen such that a signal is obtained from a label in relation to the presence or amount of analyte in the sample. The assay can be performed either without separation (homogeneous) or with separation (heterogeneous) of any of the assay compounds or products.

Homogeneous assays are exemplified by the EMIT® assay products (Syva Company, San Jose, Calif.); nephelometric and turbidimetric assays, frequently latex-enhanced; nucleic acid hybridization assays as described in EP-A2-0 070 685, assays as summarized in Boguslaski & Li (1982), Applied Biochemistry and Biotechnology, 7:401–414; and assays as those disclosed in EP-A2-0 515 194, examples 2 and 5 (incorporated herein by reference).

In a heterogeneous assay approach, the assay components usually comprise a (i) sample suspected of containing an analyte which is a specific binding partner, (ii) a first specific binding partner directly or indirectly bound, or to be bound to a solid support, which may be either a non-dispersible solid support or a particle, (iii) and a second specific binding partner directly or indirectly bound, or to be bound to a member of a signal producing system. The first and/or the second specific binding partner can be an analyte analog. The assay components and, if necessary, other reagents such as buffers, substrate solutions, etc., are generally combined either simultaneously or wholly or partially sequentially, and incubated under conditions to allow the binding reactions between the respective specific binding pair members. The solid support is then separated from the liquid phase and often washed to remove unbound reagents. Afterwards, the solid support or the liquid phase is examined for the presence of said member of a signal producing system, which is related to the presence or amount of analyte.

Separation can be achieved by any means, including without limitation, separation of a liquid phase from a solid support by filtration, microfiltration, double antibody precipitation, centrifugation, chromatography, electrophoresis, magnetic separation, and removal of a solid support (e.g. a dip stick) from a sample.

Different formats of homogeneous and heterogeneous assays are known. In a sandwich assay, the analyte is sandwiched by at least two specific binding pair members. In a competitive assay, the analyte competes usually with an analyte analog to be bound by a specific binding partner.

By way of illustration and not limitation, such assay formats in the field of immunoassays can be also characterized by the complexes formed: (i) sandwich immunoassays by the formation of "antibody< >antigen< >antibody" complexes or "antigen< >antibody< >antigen" complexes; (ii) indirect immunoassays by the formation of "antigen< >antigen-specific antibody (analyte)< >anti-antibody" complexes; and (iii) competitive immunoassays by the formation of "antibody< >antigen" complexes, "antibody< >hapten" complexes or "antibody< >analyte analog" complexes.

In a typical competitive heterogeneous assay a solid support having an antigen-specific antibody bound thereto is contacted with a medium containing the sample and an analyte analog conjugated to a detectable label such as an enzyme (the "conjugate"). Analyte in the sample competes with the conjugate for binding to the antibody. After separating the solid support and the medium, the label activity of the solid support or the medium is determined by conventional techniques and is related to the amount of analyte in the sample. Alternatively, the antigen analog may be bound to the solid support and the antigen-specific antibody is labeled.

In a typical homogeneous or heterogeneous sandwich immunoassay, a sandwich complex is formed in an assay medium. The complex comprises the analyte, a first antibody (monoclonal or polyclonal) that binds to the analyte and a second antibody (monoclonal or polyclonal) that binds to the analyte or a complex of the analyte and the first antibody. Subsequently, the sandwich complex is detected and is related to the amount of analyte in the sample. The sandwich complex is detected by virtue of the presence in the complex of a label wherein either or both the first antibody and the second antibody are associated with labels.

In a homogeneous assay without any separation step, but also in a heterogeneous assay, latex particles may be used as label(s), and particle complexes are determined, e.g., by nephelometric or turbidimetric methods. The labels may be also substances which are brought into a distance from each other which permits or prevents an interaction, in particular an energy transfer, between the substances, and the extent of the interaction is measured. Such an energy transfer can take place by means of short-lived molecules, e.g. singlet oxygen, short-range radiation, e.g. radioactive β radiation, and/or energy transfer in accordance with Förster or non-Förster mechanism. Further, the activity of said substances can be augmented or inhibited by other substances leading to a measurable change in signal, for example change in the intensity or polarization of the emitted light, inhibition of or increase in enzyme activities and/or change in fluorescence behaviour.

In case of a heterogeneous sandwich assay, a first specific binding partner is bound to a solid support and a second specific binding partner is bound to a label. After one or more incubation steps, the solid support is separated from the liquid phase and any sandwich complexes bound to the solid support are determined. In a variation of said sandwich assay, the sample in a suitable medium is contacted with the labeled specific binding partner and incubated for a period of time. Then, the medium is contacted with a solid support to which is bound the second specific binding partner. In another variation of the above, the sample, the first specific binding partner bound to a solid support and the labeled specific binding partner are combined in a medium and incubated in a single incubation step.

Sandwich assays find use for the most part in the detection of polyvalent analytes; the preferred assays to detect monovalent analytes are competitive assays. The present invention has application to all of the above assays.

"Wholly or partially sequentially" means that if the sample and the other agents utilized in an assay are combined other than concomitantly (simultaneously), or one or more may be combined with one or more of the remaining agents to form a subcombination. Subcombination and remaining agents can then be combined.

"Polysaccharide" means a carbohydrate containing three or more non-modified or modified monosaccharide units, such as, e.g., dextran, starch, glycogen, inulin, levan, mannan, agarose, galactan, carboxydextran or aminodextran; the polysaccharide can be hydrolyzed into the simpler monosaccharide units. Examples of polysaccharides by way of illustration and not limitation are dextran, starch, glycogen, polyribose and the like.

"Dextran" means a polysaccharide consisting of linear 1-carbon to 6-carbon linked (98%) glucose units; a polymerized glucose.

The term "functional groups" includes carboxylic acids, aldehydes, ketones, amino groups, cyano groups, ethylene groups, hydroxyl groups, thiols, carboxamides, carbamates, carboxylic acid esters, sulfonic acids, sulfonic acid esters, phosphoric acids, phosphoric acid esters, ureas, phosphoramides, sulfonamides, ethers, sulfides, thioethers, olefins, acetylenes, amines, nitriles, halides, and the like.

"Amine reactive functional group" means a functionality reactive with an amine functionality, usually by virtue of nucleophilicity or basicity of the amine, such as, for example, an aldehyde, an α-keto carboxylic acid, an epoxyl group, and the like.

Usually, two molecules are "covalently bound" or "covalently coupled", when electrons are shared by at least one atomic nucleus of the first molecule and one atomic nucleus of the second molecule.

A "coating" means at least one layer of a covering over the surface of the carrier. The coating may cover the carrier surface completely or partly; it may be a monomolecular or multimolecular layer. A successive layer means one layer is coated on top of a preceding layer. A successive layer may include the first coating layer as the carrier.

Various ancillary materials will frequently be employed in the assay. For example, buffers will normally be present in the assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

In the following, specific embodiments of the invention are described in more details:

The present invention relates to a carrier having a surface coating provided with pendent functional groups. The surface coating comprises at least two layers of polysaccharide. The polysaccharide of the first coating layer is covalently coupled to the carrier by reaction between the functional groups of the carrier and the functional groups of the polysaccharide of the first coating layer. Further, the polysaccharide of the second coating layer is covalently coupled to the first coating layer by reaction between the functional groups of the first coating layer and the functional groups of the polysaccharide of the second coating layer. Additional layers of polysaccharide with pendent functional groups may be optionally employed.

In the present invention, the polysaccharide of the first coating layer spontaneously associates with polysaccharide of the second coating layer and, optionally, with the carrier. Spontaneous association between the polysaccharide layers and between the carrier and first polysaccharide layer occurs when the functional groups of the one of polysaccharide layers are attracted to or spontaneously reacts with the functional groups of the carrier or another layer. Examples of spontaneous association include the attraction of one layer of polysaccharide to another layer of polysaccharide (or to the carrier) because the functional groups of the layers (or the first layer and the carrier) are oppositely charged. This may occur when one polysaccharide has carboxyl functional groups and the other layer is an aminodextran. Spontaneous association may also occur between a carboxylated carrier and an amino dextran due to the opposite charge of the functional groups.

Another example of a spontaneous association is the spontaneous formation of a Schiff base, which occurs when the pendent aldehyde groups of a dextran aldehyde layer associate with the amine groups of an aminodextran. The linkage may be reduced in the process of a mild reducing agent such as $NaCNBH_3$ or the like. Still another example is spontaneous association of a thiolated dextran with a halogenated dextran. This nucleophilic substitution reaction occurs spontaneously and rapidly under optimum conditions of pH (usually 8 or higher) at room temperature.

Another example of a spontaneous association is the nucleophilic substitution which occurs between pendent amino groups of a dextran amino layer and carboxy groups of a carboxydextran activated by carbodiimide. To support this reaction the —COOH containing molecule will form an acyl amino ester with N-Hydroxysuccinimide by using a carbodiimide. This molecule will react with the amino groups of an aminodextran yielding a stable amide bond.

The spontaneous association of the first layer with the carrier, or successive layer of polysaccharide with each other, leads to numerous advantages. One advantage is that the carrier may be easily coated with a first layer of polysaccharide. As an example, the reaction between a carboxylated particle and an amino dextran requires only use of carbodiimide conjugation chemistry. No linking group is necessary, which reduces the steps of preparation as well as allows for greater control of the reaction.

Similarly, the advantages of spontaneous association between polysaccharide layers are seen when the polysaccharides have opposite charges, such as a carboxylated dextran and an amino dextran, or when the functional groups of the layers spontaneously react. Again, the coupling of polysaccharides which spontaneously associate allows for a simple preparation without the need of a bifunctional linking group such as gluteraldehye. This allows for better control of the reaction while ensuring a substantially complete covering of polysaccharide on a carrier or on a preceding polysaccharide layer.

In one embodiment of the present invention, a carrier with pendent functional groups is provided by a carrier, such as a polystyrene particle, with a carboxylated surface (amine reactive functional group). The surface coating comprises at least two layers of polysaccharide. One coat has amine functional groups and the other coat has amine-reactive functional groups. The polysaccharide of the first coating layer is covalently coupled to the carrier by reaction between amine-reactive functional groups of the carrier (i.e. carboxyl groups) and amine groups of the polysaccharide of the first coating layer. The polysaccharide of the second coating layer is covalently coupled to the first coating layer by reaction between the amine functional groups of the first coating layer and the amine-reactive functional groups of the polysaccharide of the second coating layer. Equally prefered is a carrier which has amine functional groups, and the first polysaccharide layer has amine reactive functional groups, the second polysaccharides layer has amine reactive functional groups and subsequent layers alternate between the two polysaccharides.

Amine-reactive functional groups on the carrier shall be accessible to covalently bind the amine groups of the polysaccharide of the first coating layer to the carrier, or alternatively, the amine functional groups on the carrier shall be accessible to covalently bind the amine-reactive groups of the polysaccharide of the first coating layer to the carrier.

Another embodiment of this invention involves a carrier wherein the polysaccharide of the first coating layer is an aminodextran. An aminodextran is a derivatized glucose polymer with amino groups having a molecular weight of about 10,000 to about 2,000,000, preferably about 500,000. Aminodextran can be prepared in small and large scale according to the instructions of U.S. Pat. No. 5,707,877, columns 18–20, and U.S. Pat. No. 5,639,620, columns 21 and 22 or as provided herein.

Still another embodiment of this invention involves a carrier wherein the polysaccharide of the second coating layer is dextran with amine-reactive functional groups selected from the group consisting of aldehydes, carboxyl groups, or epoxy groups having a molecular weight similar to that of amino dextran.

Another specific embodiment of the present invention is a carrier wherein the polysaccharide of the first coating layer is a dextran with amine-reactive functional groups and the polysaccharide of the second coating layer is preferably an aminodextran.

A method is preferred wherein carbodiimide conjugation chemistry is used for the coupling of the polysaccharide of the first coating layer to said carrier. Another method is preferred wherein the coupling of the polysaccharide of the second coating layer to the first coating layer is done in the presence of a mild reducing agent, such as, e.g., sodium cyanoborhydride. Alternatively, a method can be used wherein carbodiimide conjugation chemistry is used for the coupling of the polysaccharide of the second coating layer to the first coating layer. A particularly preferred method to prepare a carrier according to the present invention is a method wherein the specific binding partners are covalently bound to the surface coating by reaction between the pendent functional groups of the surface coating and functional groups of the specific binding partners.

The carrier may be washed between the reaction steps to remove unbound compounds and/or to exchange the reaction medium.

To illustrate this invention, and referring now to FIG. 1A, the coating of carboxylate polystyrene particles with a diameter of about 200 nm are described. Briefly, carboxylate particles are coated first with aminodextran (AmDex) molecules (having multiple amino groups per AmDex molecule) using carbodiimide (EDAC) conjugation chemistry. The presence of opposite charges on the bead surface (—COO$^-$) and on the AmDex (—N$^+$H$_3$) attract each other and in the presence of a relatively large excess of AmDex the particle surface is rapidly and effectively covered by AmDex molecules, even in the absence of EDAC. In this fashion, the polysaccharide spontaneously associates with the particles. This phenomenon leads to an increased concentration of amino groups near to the surface of the carboxylate particles and which in turn improves the efficiency of EDAC conjugation method. Also, the presence of a dextran layer on the surface of the carboxylate particles will minimize the particle aggregation problem, generally observed when the carboxylate particles are exposed to EDAC at pH below 7.0. Adding EDAC at this point activates the —COOH groups on the particle, which then react with —NH$_2$ groups on AmDex leading to the formation of a chemically stable amide bond. Only a fraction of the amino groups from the AmDex molecule are involved in forming the covalent amide bond and the remaining amino groups are available for reactions with various reactive groups (for example aldehyde groups or carboxyl groups). Such particles are referred to as single coated amino beads (C-bead-AmDex). Unlike introducing amino groups by using small molecular weight diamines (ethylene diamine, propylene diamine, etc.) and EDAC, using AmDex eliminates the need for close monitoring of the pH of the reaction, thus simplifying the procedure significantly.

The second layer of polysaccharide can be introduced by reacting the C-bead-AmDex reagent with a relatively large excess of dextran aldehyde (DexAI) having multiple aldehyde groups per DexAI molecule. This spontaneous reaction is a form of spontaneous association of the polysaccharide layers. A fraction of the aldehyde groups on a DexAI molecule react with amino groups on the C-bead-AmDex reagent forming shiff-base, which then can be reduced with a mild reducing agent such as cyanoborohydride (NaBH$_3$CN) to form a chemically stable carbon-nitrogen chemically stable bond. Since the reduction of free aldehyde groups by NaBH$_3$CN is negligible, the resulting coated particles have reactive aldehyde groups on the surface and can be reacted with amino group containing molecules (such as antibodies or other proteins or further AmDex molecules). It shall be noted that there are multiple amino groups on the surface of the C-beads-AmDex reagent and multiple aldehyde groups on the DexAI molecule, which most likely leads to multipoint reaction within a molecule and random crosslinking of these two hydrogel layers, resulting in a "shell" and improved stability of the coat. This reagent is referred herein as double coated aldehyde particles (C-bead-AmDex-DexAI).

The conjugation of a specific binding partner, such as an antibody (or other amino group containing molecules), to the C-bead-AmDex-DexAI reagent can be performed by reductive amination method. Purified antibody in native form (not modified) is simply incubated with C-bead-AmDex-DexAI reagent in presence of NaBH$_3$CN for a certain period of time, preferably at room temperature or at 37° C. The remaining free aldehyde groups are capped (various molecules can be used for this purpose, for example carboxymethyl oxime or carboxymethoxylamine, etc.). Finally the particles are washed several times with an appropriate buffer (e.g. Tris buffer; pH 8.0). After resuspending the pellets by sonication the particles are preferably stored at 1 mg/ml concentrations in an appropriate buffer.

The present invention includes carriers with more than two coating layers of hydrogels (for example: Bead-ADx-DexAI-ADx; Bead-ADx-DexAI-ADx-DexAI; Bead-ADex-CEDex-ADx; Bead-ADex-CEDex-ADx-CEDex; and so on)

wherein a surface with similar properties to the double coated surface is created. Preferred are carriers with 2 to 10 polysaccharide coating layers, particularly preferred are carriers with 2 to 5 polysaccharide coating layers, the most preferred carriers are carriers with 2 or 3 polysaccharide coating layers. They can be prepared by analogy with the above disclosed methods or the methods described in details in the examples.

Figure 1B:
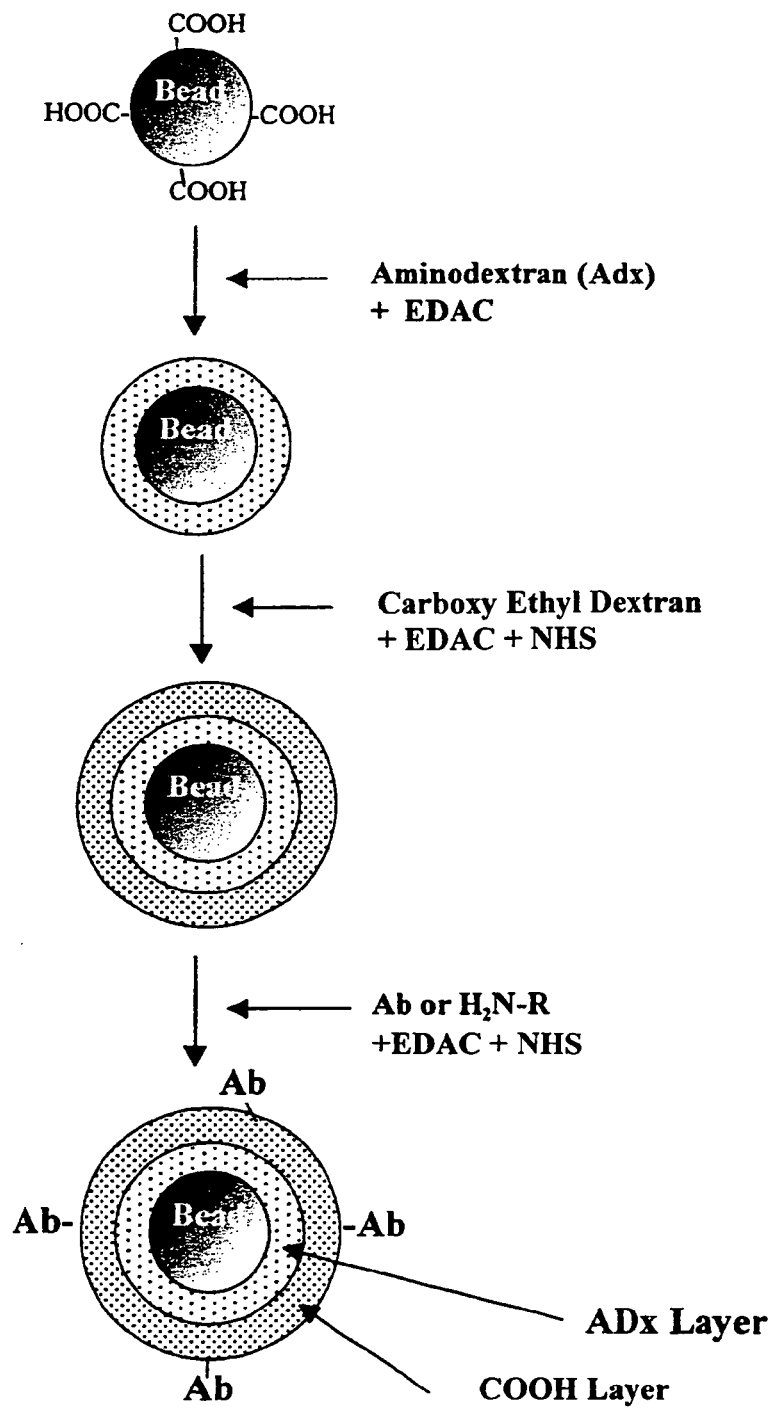

Similarly, in FIG. 1B, synthesis of a particle coated with one layer of aminodextran and one layer of carboxylethyl dextran is shown.

The carriers according to the present invention can be used for in vitro and/or in vivo diagnostic methods. The carriers are particularly useful in a method for the quantitative and/or qualitative determination of an analyte. Preferred methods for the quantitative and/or qualitative determination of an analyte according to the present invention are homogeneous or heterogeneous assays, wherein one or more specific binding partners may be bound to a carrier according to the invention. The assays can be sandwich assays, competitive assays or indirect assays. The carrier can have the function of a solid support and/or a label. In assays where particles are used, all particles or only a part of the particles may be a carrier according to the present invention.

A preferred method for the quantitative and/or qualitative determination of an analyte according to the present invention is an assay wherein substances are brought into a distance from each other which permits or prevents an interaction, in particular an energy transfer, between the substances, and the extent of interaction is measured. Said substances and/or one or more specific binding partners may be associated with a carrier according to the present invention. The term "substances" is to be understood as meaning members of biological and/or chemical substance classes which, when in spatial proximity, can enter into interaction with each other, e.g. in the form of energy donors and energy recipients, such as, e.g., photosensitizers and chemiluminescers (EP-A2-0 515 194; Ullman et al. (1996) Clinical Chemistry 42:1518–1526), photosensitizers and fluorophores (WO 95/06877; Bystrak et al. (1995) Anal. Biochem. 225:127–134), or radioactive iodine$^{125}$ and fluorophores (Udenfriend et al. (1985) Proc. Natl. Acad. Sci. 82:8672–8676), or fluorophores and fluorophores (Mathis, G. (1993) Clin. Chem. 39:1953–1959) or fluorophores and fluorescence quenchers (U.S. Pat. No. 3,996,345).

An interaction between the substances is to be understood, in particular, as meaning an energy transfer—that is the direct transfer of energy between the substances, e.g. by means of light or electron radiation as well as by way of reactive chemical molecules. While the energy transfer can take place from one substance to another substance, it is also possible for the energy transfer to run through a cascade of different substances.

In addition, the phrase "interaction between the substances" also encompasses processes in which the activity of a substance is inhibited or augmented by one or more different substances, for example inhibition of or increase in the enzyme activity, or the inhibition of, the increase in or change of (e.g. wavelength displacement, polarization) the light which is emitted by the affected substance.

The phrase "interaction between the substances" is also to be understood as meaning enzyme cascades. In this case, the substances are enzymes, at least one of which supplies the substrate for another enzyme, wherein, as a consequence, e.g., of the formation of "analyte-specific binding partner" or "analyte analog-specific binding partner" complexes, the enzymes are brought to a distance from each other such that the reaction velocity of the coupled substrate conversion achieves a maximum or a minimum.

An effective interaction between the substances usually takes place when these substances are spatially adjacent, that is, e.g., within a distance range of a few μm, in particular within a distance range of less than 600 nm, preferably less than 400 nm, and very particularly preferably less than 200 nm.

In a preferred embodiment of a method according to the present invention, the interaction between the substances is effected as an energy transfer, for example by means of (i) short-lived molecules, e.g., singlet oxygen (EP-A2-0 515 194; Ullman et al. (1994) Proc. Natl. Acad. Sci. 91:5426–5430; Ullman et al. (1996) Clinical Chemistry 42:1518–1526; WO 95/06877; Bystrak et al. (1995) Anal. Biochem. 225:127–134); (ii) short-range radiation, e.g., radioactive β radiation (Hart & Greenwald (1979) Molecular Immunology 16:265–267; Udenfriend et al. (1985) Proc. Natl. Acad. Sci. 82:8672–8676); (iii) and/or energy transfer in accordance with Förster (Mathis, G. (1993) Clin. Chem. 39:1953–1959; U.S. Pat. No. 5,527,684).

In another preferred embodiment of a method according to the present invention, the activity of substances is augmented or inhibited by other substances and this leads to a measurable change in signal, for example change in the intensity or polarization of the emitted light, inhibition of or increase in enzyme activities and/or change in fluorescence behaviour.

Particularly advantageous embodiments of a method according to the present invention are distinguished by the fact that one or more of said substances can be bound covalently, by way of a specific interaction via specific binding partners and/or adsorptively to a carrier according to the present invention, preferably particles, and/or are incorporated into said carrier or themselves constitute a carrier or a part thereof. In the case of a covalent bond, the substances are linked by way of a chemical bond to the carrier and/or to any possible shells or layers which coat the carrier.

A particularly preferred method is the use of the carriers of the present invention in a Luminescent Oxygen Channelling Immunoassay (LOCI™) as described in EP-A-0 515 194. In this method for the qualitative or quantitative determination of an analyte, at least one specific binding partner is bound to a carrier according to the present invention, comprising the steps of: treating a medium suspected of containing an analyte under conditions such said analyte affects the amount of a sensitizer capable in its excited state of generating singlet oxygen and a chemiluminescent compound that can come into close proximity such that singlet oxygen generated by said photosensitizer can activate said chemiluminescent compound, which subsequently produces light, and measuring said light, the amount thereof being related to the amount of analyte in said medium.

Another example of the LOCI™ method, wherein a carrier according to the present invention is used, is a method for the qualitative or quantitative determination of an analyte comprising the steps of: (A) combining either simultaneously or wholly or partially sequentially (i) a medium suspected of containing the analyte; (ii) a first specific binding partner associated with a sensitizer capable in its excited state of generating singlet oxygen; and (iii) a second specific binding partner associated with a composition comprising a chemiluminescent compound, which is a substance that undergoes a chemical reaction with singlet oxygen to form a metastabile intermediate species that can decompose with the simultaneous or subsequent emission of light; (B) allowing the formation of complexes comprising the first and the second specific binding partner, said complex formation brings said sensitizer into close proximity to said chemiluminescent compound, (C) activating the sensitizer to generate singlet oxygen; and measuring the amount of light emitted by the chemiluminescent compound, said light is directly or inversely proportional to the amount of analyte in the medium. The composition comprising the chemiluminescent compound can also comprise one or more fluorescent molecules which are excited by the activated chemiluminescent compound. The light emitted by said fluorescent molecules can be measured to determine the amount of analyte in the medium.

Further details regarding preferred assays using the carriers according to the present invention are disclosed in EP-A2-0 515 194, particularly in examples 1–8.

Another in vitro use of the carriers according to the present invention is to capture or select a species from a sample. For example, cancer cells can be easily removed from a sample by binding the cancer cells to antibodies attached to magnetic particles prepared according to the present invention, and then performing a magnetic separation step. Similarly, enzymes can be bound to a carrier according to the present invention which allows them to be easily removed from the reaction mixture or to be used in a continuous flow process. Another in vitro application for carriers according to the present invention is to use antibodies, lectins, oligonucleotides or other specific binding partners bound to such a carrier to affinity-purify compounds which are specifically bound by said specific binding partner.

A carrier according to the present invention can also be applied in vivo to an animal or a human, particularly if applied in a pharmaceutically acceptable medium. It is well-established (e.g. WO 96/04017, WO 96/27394, EP-A1-0 525 199) to use magnetic and non-magnetic particles for imaging purposes, e.g. to detect "disease sites" in vivo such as tumors, blood clots or inflammation sites or to measure the blood flow in an organ or the metabolism activity of an organ. Particles prepared according to the present invention are advantageous because of their hydrophilic coating which prevents unspecific aggregation of the applied particles or blood clot formation. The same advantages apply for carriers according to the present invention which can be also used for therapeutic methods, for example as toxic drug carriers, e.g. to destroy tumor cells; as implanted drug release systems, such as a insulin pump; or as stents to prevent the stenosis of a blood vessel.

EXAMPLES

| | Abbreviation Used |
|---|---|
| Ab | Antibody |
| Acc | Acceptor bead in a LOCI ™ Assay |
| AmDex (AmDx) | Aminodextran |
| Biotin-X-NHS | sulfosuccinimidyl-6-(biotinamido)-hexanoate |
| BSA | bovine serum albumine |
| B-IgG | bovine immunglobuline G |
| CEDex | Carboxylethyldextran |
| CHO | Aldehyde group |
| C-bead | Chemiluminescent bead |
| DC | double coated b ads |
| DexAl | Dextran Aldehyde |
| Dig | Digoxin |
| DMSO | dimethyl sulfoxide |
| EDO or EDAC | 1-Ethyl-3-(Dimethylpropyl)carbodiimid |
| EDTA | ethylenediamine tetraacetic acid |
| MES | 2-(N-Morpholino)ethansulfon acid |
| NaCl | sodium chloride |
| NHS | N-Hydroxysuccinimide |
| PBS | phosphate buffered saline 0.02 M NaPi, 0.14 M NaCl/pH 7.2 |
| Pi | phosphate |
| PSA | prostate specific antigen |
| S (S-Bead) | sensitizer bead for a LOCI ™ Assay |
| SC | single coated |
| Sens-Sav Beads | Streptavidin coated sensitizer beads |
| TAR-Beads | (Thioxene, Anthracene, Rubrene)-Beads |
| TRIS-HCL | tris-(hydroxymethyl)-aminomethane-hydrochloric acid |

The following examples are given to illustrate the utility of the claimed invention and are not to be taken as limiting the invention. In particular, the preparation of reagents for the LOCI™ method, and assays using the LOCI™ method, are described.

A. Preparation of Amino Dextran (AmDex)

Numerous methods of the preparation of amino dextran are known in the art. In addition, two preferred methods are provided herein.

Method 1: Hydroxypropylaminodextran ($1NH_2/7$ glucose) was prepared by dissolving Dextran T-500 (Pharmacia, Uppsala, Sweden) (50 g) in 150 mL of $H_2O$ in a 3-neck round-bottom flask equipped with mechanical stirrer and dropping funnel. To the above solution was added 18.8 g of Zn $(BF_4)_2$ and the temperature was brought to 87° C. with a hot water bath. Epichlorohydrin (350 mL) was added dropwise with stirring over about 30 min while the temperature was maintained at 87–88° C. The mixture was stirred for 4 hr while the temperature was maintained between 80° C. and 95° C., then the mixture was cooled to room temperature. Chlorodextran product was precipitated by pouring slowly into 3 L of methanol with vigorous stirring, recovered by filtration and dried overnight in a vacuum oven.

The chlorodextran product was dissolved in 200 mL of water and added to 2 L of concentrated aqueous ammonia (36%). This solution was stirred for 4 days at room temperature, then concentrated to about 190 mL on a rotary evaporator. The concentrate was divided into two equal batches, and each batch was precipitated by pouring slowly into 2 L of rapidly stirring methanol. The final product was recovered by filtration and dried under vacuum.

Method 2: Hydroxypropylaminodextran was prepared by dissolving 100-g of Dextran T-500 (Pharmacia, Uppsala, Sweden) in 500-mL of water in a 3-neck round-bottom flask with a mechanical stirrer and dropping funnel. To the solution were added 45-g sodium hydroxide, 50-mg EDTA, 50-mg $NaBH_4$, 50-mg hydroquinone, and 200 g N-(2,3-epoxypropyl) phthalimide. The mixture was heated and stirred in a 90° water bath for two hours. A small aliquot was precipitated three times from methanol and analyzed by nmr-appearance of a peak at 7.3–7.6 indicated incorporation of phthalimide. The main reaction mixture was precipitated by addition to 3.5 L of methanol and the solid was collected. The phthalimide protecting group was removed by dissolving the product above in 500-mL of 0.1 M acetate buffer, adding 50-mL of 35% hydrazine, and adjusting the pH to 3.5. The mixture was heated at 80° C. for 1 hour, the pH was re-adjusted to 3.2, and the mixture was heated for an additional half hour. An aliquot was precipitated three times in methanol. NMR showed that the phthalimide group was no longer present. The reaction mixture was neutralized to pH 8 and stored at room temperature.

The product was purified by tangential flow filtration using a 50,000 molecular weight cut-off filter, washing with water, 0.01 M HCl, 0.01 M NaOH, and finally water. The product solution was concentrated by filtration to 700-mL then lyophilized. Determination of reactive amines using trinitrobenzenesulfonate gave about 1 amine per 16 glucose residues.

B. Preparation of Dextran Aldehyde

Dextran (400 g, 500 kD) was dissolved in 1.5 L of water (Millipore), in a 4 L beaker by heating at 70° C. with overhead stirring. The dextran was added to water at 70° C. in 30–50 g portions, each portion being added after the first portion had dissolved. The overhead stirrer was set at 300–400 rpm.

The hot dextran solution was filtered through a fritted funnel (coarse) into an erlenmeyer flask and the filtered solution was poured into a 3-necked flask preequilibrated at 70° C. The beaker was rinsed with 50 mL of hot water, which was filtered through the fritted funnel into the erlenmeyer. This filtrate was added to the is reaction mixture.

The funnel was removed from the side neck of the flask and a dual entry Claisen distillation adapter was inserted in its place. The overhead stirrer was started and set at 600–700 rpm and the temperature of the dextran solution was allowed to reach 70° C. The temperature of the oil bath was set at 72–75° C. The reaction was conducted under argon. The solution of $Zn(BF_4)_2$, (400 mL, 25 wt % in $H_2O$, pH 1.8±0.2) was poured into the flask containing the dextran solution using a funnel on the Claisen adapter. The funnel was removed from the Claisen adapter and replaced with an addition funnel (500 mL capacity) with a pressure equalizing side arm.

Allyl glycidyl ether (500 mL of the 1.5 L to be added) was added into the addition funnel (in 3×500 mL portions) at 8–10 mL/min, while the reaction temperature was maintained at 70±2° C. The addition of the allyl glycidyl was continued until all of the 1.5 L were added. Then, the temperature of the reaction mixture was increased to 80° C. The reaction was allowed to proceed for 12–13 h at 80° C. under argon, while being continuously stirred (600–700 rpm).

The reaction vessel was removed from the oil bath and the reaction mixture was allowed to cool to 30° C. The cooled reaction mixture was then poured into 6.0 L of water (Nalgene bucket with spigot) and stirred manually. The diluted reaction mixture was purified by ultrafiltration using a Microgon tangential flow diafiltration system. The allyloxy dextran was concentrated to 1.0–1.5 L.

An aliquot (50 mL) of the filtrate was removed and freeze dried for analytical purposes. The remaining solution of allyloxy dextran in water was stored at 4° C. and used for the next step. The $^1H$ and $^{13}C$ nuclear magnetic resonance (NMR) spectra of the above allyloxy dextran was consistent with the expected product.

The allyloxy dextran was subjected to ozonolysis in a 4.0 L beaker equipped with an overhead stirrer. The mixture was stirred at 300–350 rpm and allowed to attain room temperature. Ozone was generated by an ozonator and was added by means of a gas bubbler immersed into the solution of allyloxy dextran at a pressure of 9.0 psi and a flow rate of 2.0 LPM (liters per minute). Ten mL of heptanol was added as an antifoamer. The reaction was monitored by $^{13}C$-NMR; the disappearance of the olefinic resonances at 118 and 134 ppm was used as an indication for the completion of the reaction. The ozone addition was continued for 5–6 h. The reaction mixture was cooled to around 10° C. To this was added 50 mL of dimethyl sulfide and stirring under an argon atmosphere was continued for 10 h. The reaction mixture was allowed to attain room temperature while being stirred (300–350 rpm) over this time. The resulting dextran aldehyde was purified by Microgon ultrafiltration.

C. Preparation of carboxyethyldextran (CEDex)

Ten grams of undried dextran T-500 was dissolved in 40-mL water. Twenty-mL of 10 N sodium hydroxide was added followed by 5.3-g acrylamide in 40-mL water. The mixture was stirred at room temperature until homogeneous and then placed in a 45 degree water bath with magnetic stirring. After 24 hours at 45 degrees the product was precipitated by slow addition to 3 volumes of vigorously stiffing ethanol. The ethanol liquors were decanted, the precipitated product dissolved in 100-mL water, and pre-cipitated a second time from 3 volumes of ethanol. After decanting the liquor, the product was dissolved in water and the pH adjusted to 7.3 with concentrated hydrochoric acid. The volume was made up to 100-mL with water and the solution stored in the refrigerator.

D. Preparation of C-28 thioxene

To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with $CH_2Cl_2$ (400 mL). The $CH_2Cl_2$ solution was washed with 1 N aqueous NaOH (2×), $H_2O$, and brine, was dried over $Na_2SO_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-($C_{14}H_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at −30° C. under argon. The reaction mixture was gradually warmed to 0° C. over 1 hr and stirred for another 30 min. The resulting mixture was poured into a mixture of ice water (800 mL) and ethyl acetate (250 mL). The organic phase was separated and the aqueous phase was extracted with ethyl acetate (3×). The combined organic phases were washed with $H_2O$ (2×), brine and were dried over $MgSO_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane)

afforded 24.7 g (50%) of the benzoin product (LSIMS ($C_{42}H_{69}NO_2$): [M-H]$^+$ 618.6, $^1$H NMR (250 MHz, CDCl$_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCI (100 mL, 788 mmol). The reaction solution was heated at reflux for 23 hr under argon before being cooled to room temperature. To this was added additional TMSCI (50 mL, 394 mmol); and the reaction solution was heated at reflux for another 3 hr. The resulting solution was cooled and was made basic with cold 2.5N aqueous NaOH and was extracted with CH$_2$Cl$_2$ (3×). The combined organic layers were washed with saturated aqueous NaHCO$_3$ (2×) and brine, was dried over Na$_2$SO$_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.5 g (60%) of the C-28 thioxene as an orange-yellow oil (LSIMS ($C_{44}H_{71}NOS$): [M-H]$^+$ 661.6, $^1$H NMR (250 MHz, CDCl$_3$) was consistent with the expected C-28 thioxene product 2-(4-(N,N-di-($C_{14}H_{29}$)-anilino)-3-phenyl thioxene.

E. Preparation of Chemiluminescer Beads (TAR Beads)

A 10% solution of carboxylated latex beads (Seradyn) (120 mL) was heated to 93° C. in a three-neck round bottom flask, and then was mixed with 166 mL ethoxyethanol, 336 mL ethylene glycol, and 12 mL of 0.1 M NaOH. A mechanical stirrer and a thermometer were added and the mixture was brought to 95° C. with stirring and then was stirred for an additional 40 min. In a separate flask, 2.45 g of C-28 thioxene, 191.8 mg of 2-chloro-9,10-bis(phenylethynyl)anthracene, and 323.9 mg of rubrene were mixed in 264 mL of ethoxyethanol and the mixture was heated to 95° C. with stirring until dissolved. The dye solution was poured into the bead solution and was stirred for 20 min. at 95° C. and then was allowed to cool slowly to about 47° C. and filtered through a 43 micron polyester filter. The beads were washed by tangential flow filtration using a Microgon apparatus with a 0.05 micron filter. After priming of the system with wash solvent (1:2 v/v ethoxyethanol:ethylene glycol), the dyed bead mixture was added. The mixture was concentrated to about 20 mg/mL and then was washed with 6 L of wash solvent and 4.8 L of 10% v/v ethanol in water adjusted to pH 10 with NaOH. The beads were concentrated to about 50 mg/mL during the wash, and then were finally stored at 4° C. protected from light. Final concentration was determined by weight after evaporating an aliquot to dryness.

F. Preparation of Silicon tetra-t-butyl phthalocyanine

Sodium metal, freshly cut (5.0 g, 208 mmol), was added to 300 mL of anhydrous methanol in a two-liter, 3-necked flask equipped with a magnetic stirrer, reflux condenser, a drying tube and a gas bubbler. After the sodium was completely dissolved, 4-t-butyl-1,2-dicyanobenzene (38.64 g, 210 mmol, from TCI Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr while the stream of ammonia gas continued during the course of the reaction, as solid started to precipitate. The resulting suspension was evaporated to dryness (house vacuum) and the residue was suspended in water (400 mL) and filtered. The solid was dried (60° C., house vacuum, P$_2$O$_5$). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical Company) was added with a syringe to the stirred solution over a period of 10 minutes. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., P$_2$O$_5$). The solid material was placed in a 1-L, round bottom flask and concentrated sulfuric acid (500 mL) was added with stirring. The mixture was stirred for 4 hr at 60° C. and was then carefully diluted with crushed ice (2000 g). The resulting mixture was filtered and the solid was washed with 100 mL of water and dried. The dark blue solid was transferred to a 1-L, round bottom flask, concentrated ammonia (500 mL) was added, and the mixture was heated and stirred under reflux for 2 hr, was cooled to room temperature and was filtered. The solid was washed with 50 mL of water and dried under vacuum (house vacuum, 60° C., P$_2$O$_5$) to give 12 g of product silicon tetra-t-butyl phthalocyanine as a dark blue solid. 3-picoline (12 g, from Aldrich Chemical Co.), tri-n-butyl amine (anhydrous, 40 mL) and tri-n-hexyl chlorosilane (11.5 g) were added to 12 g of the above product in a one-liter, three-necked flask, equipped with a magnetic stirrer and a reflux condenser. The mixture was heated under reflux for 1.5 hr. and then cooled to room temperature. The picoline was distilled off under high vacuum (oil pump at about 1 mm Hg) to dryness. The residue was dissolved in CH$_2$Cl$_2$ and purified using a silica gel column (hexane) to give 10 g of pure product di-(tri-n-hexylsilyl)-silicon tetra-t-butyl phthalocyanine as a dark blue solid. (LSIMS: [M-H]$^+$ 1364.2, absorption spectra: methanol: 674 nm ($\epsilon$ 180,000): toluene 678 nm, $^1$H NMR (250 MHz, CDCl$_3$): δ: –2.4(m, 12H), –1.3(m, 12H), 0.2–0.9 (m, 54H), 1.8(s, 36H), 8.3(d, 4H) and 9.6 (m, 8H) was consistent with the above expected product.

G. Preparation of Sensitizer Beads Dyed with Silicon tetra-t-butyl phthalocyanine (S-Bead)

The sensitizer beads were prepared placing 600 mL of carboxylate modified beads (Seradyn) in a three-necked, round-bottom flask equipped with a mechanical stirrer, a glass stopper with a thermometer attached to it in one neck, and a funnel in the opposite neck. The flask had been immersed in an oil bath maintained at 94±1° C. The beads were added to the flask through the funnel in the neck and the bead container was rinsed with 830 mL of ethoxyethanol, 1700 mL of ethylene glycol and 60 mL of 0.1N NaOH and the rinse was added to the flask through the funnel. The funnel was replaced with a 24–40 rubber septum. The beads were stirred at 765 rpm at a temperature of 94±1° C. for 40 min.

Silicon tetra-t-butyl phthalocyanine (10.0 g) was dissolved in 300 mL of benzyl alcohol at 60±5° C. and 85 mL was added to the above round bottom flask through the septum by means of a syringe heated to 120±10° C. at a rate of 3 mL per min. The remaining phthalocyanine solution was then added as described above. The syringe and flask originally containing the phthalocyanine was rinsed with 40 mL of benzyl alcohol and the rinse was transferred to the round-bottom flask. After 15 min 900 mL of deionized water and 75 mL of 0.1N NaOH was added dropwise over 40 min.

The temperature of the oil bath was allowed to drop slowly to 40±10° C. and stirring was then discontinued. The beads were then filtered through a 43 micron polyester filter and subjected to a Microgon tangential flow filtration apparatus (Microgon Inc., Laguna Hills, Calif.) using ethanol:water, 100:0 to 10:90, and then filtered through a 43 micron polyester filter.

H. Preparation of Hydroxypropylaminodextran-Coated Sensitizer Beads (S-Bead-AmDex)

A solution of hydroxypropylaminodextran was prepared at 2 mg/mL in 50 mM MES (pH 6). One hundred fifty (150) mg phthalocyanine sensitizer beads in 7.5 mL water was added dropwise to 7.5 mL of the hydroxypropylaminodextran solution while vortexing. One hundred eighty eight (188) µL of EDAC solution (80 mg/mL) in water was added to the coating mixture while vortexing. The mixture was incubated overnight at room temperature in the dark. The mixture was diluted with 12 mL water and centrifuged. The supernatant was discarded and the bead pellet was suspended in 40 mL water by sonication. The beads were washed 3 times with water (40 mL per wash) by repeated centrifugation and suspension by sonication. The final pellet was suspended in 5 mL water.

I. Preparation of Aminodextran Coated Chemiluminescent Beads (C-bead-AmDex)

The C-bead-AmDex reagent was prepared by mixing 1 ml (22 mg/ml) of chemiluminescent carboxylate beads (C-bead-COOH) (Seradyn) with 1 ml of 20 mg/ml A Hydroxypropylaminodextran (MW 500K) in 0.05M MES/pH 6.0 in presence of 3.8 mg/ml EDAC. After incubating this mixture for 16 hours at room temperature, in dark the beads were washed once with 2 ml of 0.05M MES/pH 6.0, then with 6 ml of 0.05M MES, 1.0M NaCl/pH 6.0. Finally the beads were resuspended in 1 ml of 0.05M MES/pH 6.0 to get 22 mg/ml C-bead-AmDex. Washing was performed by centrifugation method (using Sorval RC-5B Plus centrifuge or Ependorf centrifuge-5415 C) and pellets were resuspended by sonication (using Branson Sonifier450).

J. Coating of C-bead-AmDex with Dextran Aldehyde to get the Aldehyde Reactive Groups Containing Double Coated Beads (C-bead-AmDex-DexAI)

The C-bead-AmDex-DexAI was prepared by mixing 1 ml of 20 mg/ml DexAI (MW 500K, prepared in house) and 1 ml of 22 mg/ml C-bead-AmDex in 0.05M MES/pH 6.0 in presence of 2 mg/ml NaBH$_3$CN. After incubating at 37° C. for 20 hours (in dark), the beads were washed once with 4 ml and then with another 5 ml of MES buffer. Finally the beads were resuspended in 0.5 ml of 0.05M MES, 0.4% Tween-20/pH 6.0 to get about 40 mg/ml C-bead-AmDex-DexAI concentration.

K. Labelling of the C-bead-AmDex-DexAI Reagent with Anti-Digoxin or Anti-TSH Abs Antibody labeled beads (C-bead-AmDex-DexAI-Ab) were prepared by mixing equal volumes of Ab solutions (0.15 mg/ml anti-Dig or 20 mg/ml anti-TSH in 0.05M MES/pH 6.0) and 40 mg/ml C-bead-AmDex-DexAI in 0.05M MES, 0.4% Tween-20/pH 6.0 in presence of 0.5 mg/ml NaBH$_3$CN. After incubating at 37° C. (3 hours for anti-Dig beads and 36 hours for anti-TSH beads) the remaining aldehyde groups were capped with 0.08M CMO (carboxymethyl oxime or carboxymethoxylamine) for 90 minutes at 37° C. Finally the beads were washed 34 times with appropriate buffer (anti-Dig beads with BSA containing Tris buffer/pH 8.0 and the anti-TSH beads with BSA and zwittergent detergent 3–14 containing Tris buffer/pH 8.0). After resuspending the pellets by sonication the beads were stored at 1 mg/ml concentrations.

L. Preparation of carboxyethyldexytran (CEDex) TAR Beads

Hydroxpropyl aminodextran beads prepared as described above are coated with carboxylethyldextran in the presence of crosslinking reagents EDC and NHS. 100 mg beads in 50 mM MES buffer, pH 5.0–9.0 (10 mg beads/ml) are incubated with EDC (1–4 mg from a stock solution: 20 mg/ml in 50 mM MES buffer, freshly prepared) and NHS (1.2–4.8 mg from a stock solution: 20 mg/ml in 50 mM MES buffer, freshly prepared). Single coated aminodextran beads are incubated over night at room temperature with different amounts of CEDex. The bead/CEDex ratio is varied from 1:1 to 200:1. The preferred standard ratio is 5:1, e.g. 10 mg beads and 2 mg CEDex. The reaction is carried out at room temperature on a rolling-mixer. After reaction the beads are washed and rebuffered in 50 mM MES buffer, pH 5.0 by centrifugation.

M. Coupling of CEDex Beads to Anti-PSA Antibody

The generated double coated beads can be used for coupling antibody, antigen, peptides and/or recombinant proteins. As an example the beads are coated with anti-PSA antibodies for the determination of prostate specific antigen.

Various amounts of antibody (250, 500 and 100 µg/10 mg bead, antibody 92-283/029 from Dade Behring Marburg GmbH) have been coupled to 10 mg CEDex-Beads. The data (not shown) indicates that 250 µg Ab is sufficient for a powerful PSA assay. Basically, the optimal amount has to be evaluated for each assay.

467 µL DC-CEDex-COOH bead solution (conc. 21.4 mg/mL), 40 µL EDC (10 mg/mL EDC in MES buffer), 48 µL NHS (10 mg/mL NHS in MES buffer) and 20 µL Tween 20 (10% Tween 20, surfact amps 20) are mixed and incubated for 15 minutes at room temperature. After 15 minutes incubation time 325 µL MES buffer and 100 µL antibody solution (250 µg antibody in MES buffer) are added and the mixture is incubated for 3–16 hours at room temperature on a rolling mixer. The coated beads are purified by centrifugation (centrifugate 30 minutes at 16.000 rpm at 10° C. [Beckmann rotor 80Ti/10 mL centrifuge bottles], discard supernatant, add 1 mL MES buffer, vortex and sonicate (Sonifier 250 in watercooled cuphorn, 2×5 Pulse, Output:4, DC 50%), add 2 mL MES buffer, centrifuge (see above). discard supernatant and add 0.95 mL buffer (0.1 M Tris-HCL, 0.3 NaCl, 25 mM EDTA, 1 mg/mL BSA, pH 8.0)

N. Preparation of Biotinylated Anti-PSA Antibody

572 µL anti-PSA antibody (4 mg/mL antibody (92-284/03, Dade Behring Marburg GmbH) in 0.1 M NaHCO$_3$) are mixed with 7.3 µL Biotin-X-NHS from Pierce Chemical Co. (5 mg/mL in DMSO). After an incubation time of 2 hours the reaction mixtures are purified on PD 10-column with PBS.

These anti-Dig, anti TSH and anti-PSA antibody labeled chemiluminescent beads (prepared by double coating labeling chemistry) were tested for their performances in LOCI™ assays.

The serum to serum variations (or matrix effect) for these beads were tested by the following procedure: anti-Dig antibody labeled chemibeads and digoxin (or digoxigenin) labeled sensitizer beads were reacted together to form the C-bead-Ab$_{Dig}$*Dig-S-bead complexes, then the LOCI™ signal was generated by repetitive illumination of these bead complexes and counting the emitted photons. The results are presented in FIG. 2 and FIG. 3.

Figure 2:
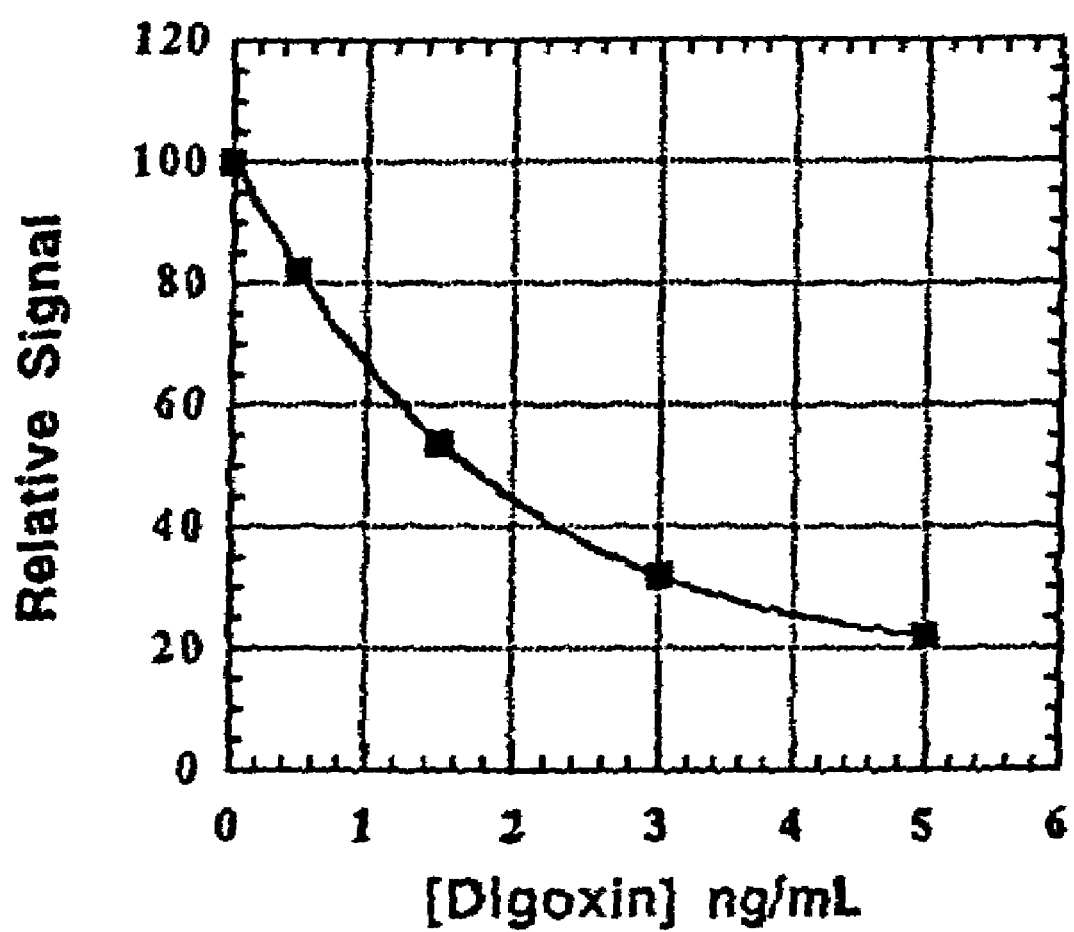
FIG. 2 depicts a typical standard curve for a LOCI™ digoxin assay.
Figure 3:
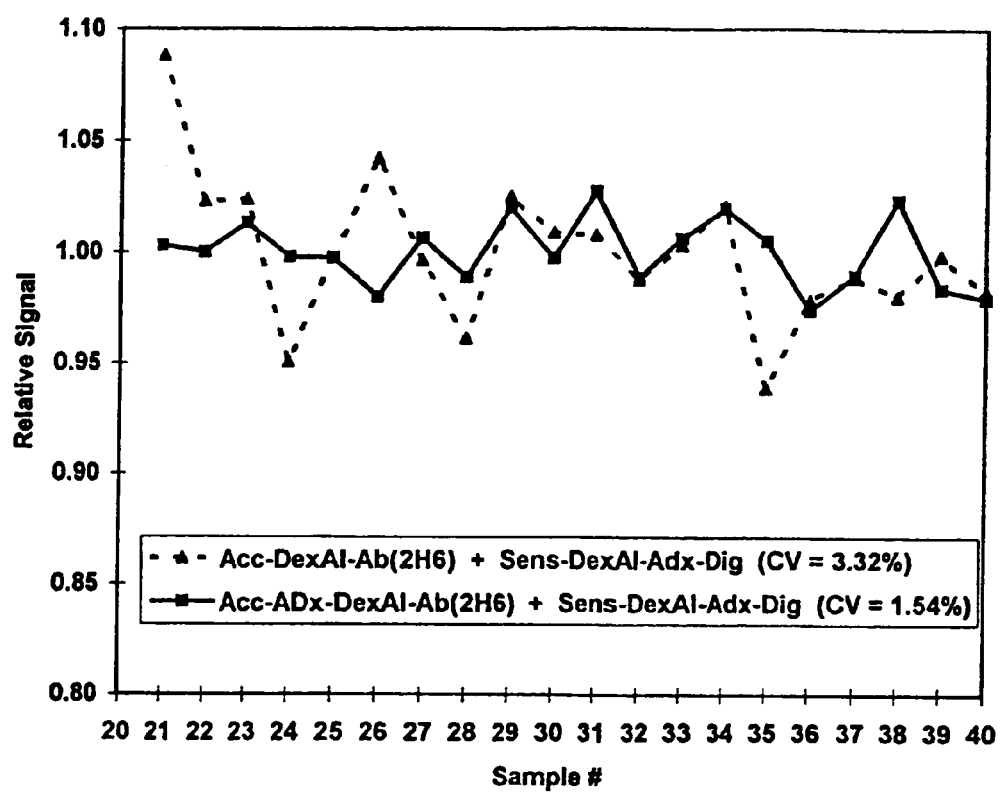
FIG. 3 depicts the results of a LOCI™ digoxin assays using a carrier of the present invention compared to a LOCI™ assay using a carrier with a single coat of polysaccharide.

FIG. 2 shows a typical course for a LOCI™ digoxin assay. FIG. 3 shows the results of a LOCI™ TSH assay comparing chemiluminescent beads double coated in accordance with the present invention (Acc-AmDex-DexAI-Ab) and beads coated with a single coat of Dextran Aldehyde (Acc-Am-Dex-DexAI-Ab). The assay was initiated by mixing 20 µl of 0.5 mg/ml C-bead $Ab_{Dig}$ reagent and 360 µl of standard LOCI™ buffer. After incubating this mixture for 108.5 seconds at 37° C., 40 µl of 0.1 mg/ml S-bead-Dig reagent and 580 µl of standard LOCI™ buffer were added and the assay mixture was incubated further for 170 seconds at 37° C. Finally, these tubes were illuminated for 1 second with 680 nm light source and the emitted photons were counted for 1 second (after shutting off the illumination light). These illumination and counting procedures were repeated 10 times (10 cycles).

As can be seen in FIG. 3, the serum to serum variation was better (CV=1.54%) using the beads prepared by the double coating chemistry. The reference bead was anti-Dig antibody labeled chemibead but had a single coat of dextran and serum to serum variation was significantly higher (CV=3.32%).

Figure 4:
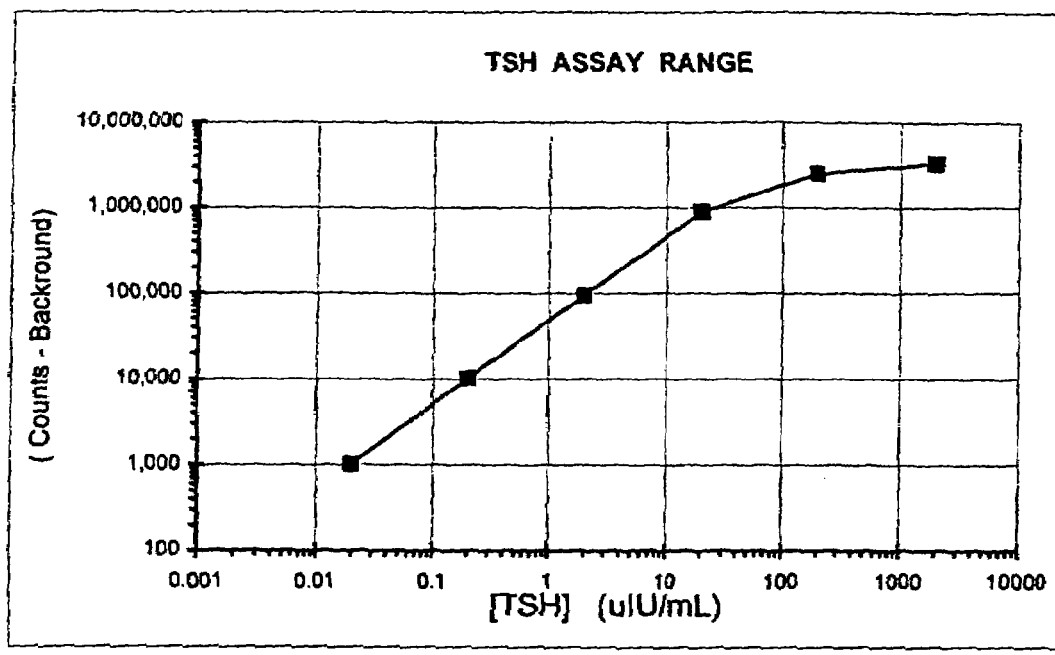
FIGS. 4, 5 and 6 depict the results of a LOCI™ TSH assay using the carriers of the present invention.
Figure 4:
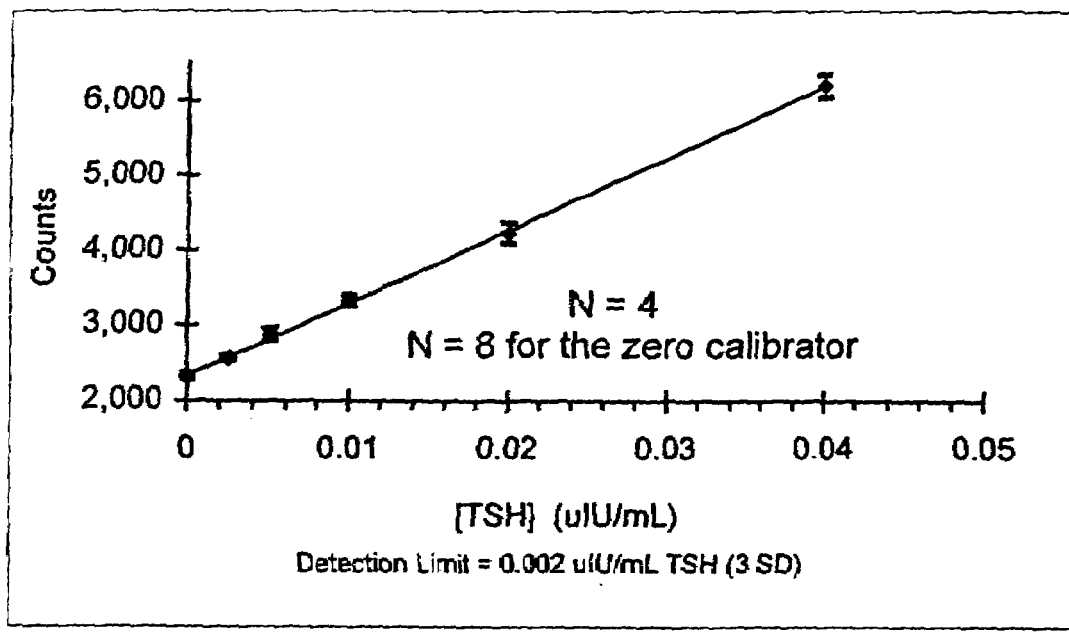

FIG. 4 shows a typical standard curve for TSH LOCI™ assay. Chemilumnescent beads were labeled with antibody to the β-chain of TSH molecule ($Ab_2$) and the second antibody (specific to the β-chain of TSH molecule, but different and not-competing epitope used for $Ab_2$) was biotinylated ($Ab_1$-biotin). The assay was performed by mixing 50 µl sample or TSH calibrators with 25 µl of 50 g/ml C-bead-$Ab_2$ and 25 µl of 6.4 µg/ml $Ab_1$-biotin reagents in LOCI™ buffer. This assay mixture was incubated for 7.3 minutes at 37° C., then 50 µl of 0.4 mg/ml S-bead-Streptavidin and 750 µl of buffer were added and the incubation at 37° C. was continued for extra 7.1 minutes. Finally, these assay tubes were illuminated for 1 second with 680 nm light source and the emitted photons were counted for 1 second (after shutting off the illumination light). These illumination and counting procedures were repeated 6 times (6 cycles).

Figure 5:
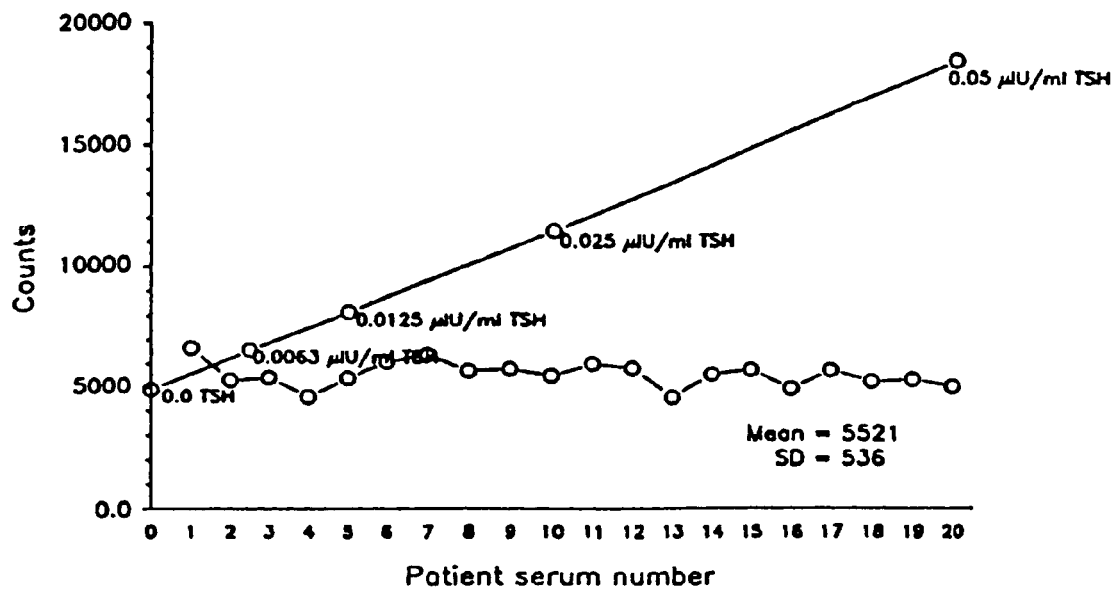
Figure 5:
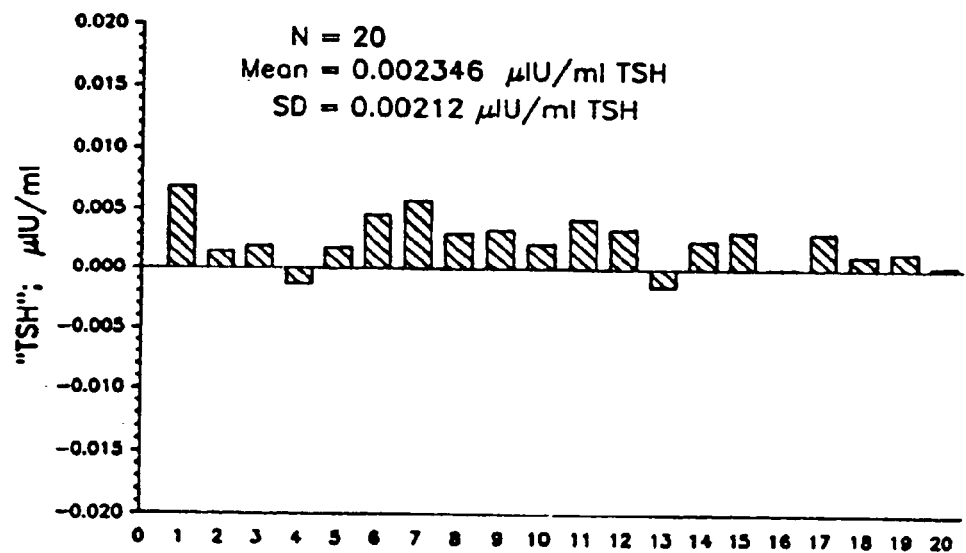

FIG. 5 shows the results of an experiment to investigate the effect of non-specific binding to LOCI™ particles which produces the matrix effect. Serum samples from 20 hypophysectomized patients (TSH concentrations in these serum samples was reported to be equal or nearly equal to 0.0 µIU/ml) were tested in TSH LOCI™ assay using C-bead-$Ab_2$ reagent prepared by double coating chemistry. The assay protocol was same as described for FIG. 4. These results indicated that matrix effect was largely eliminated due to the double coating of the LOCI™ chemibeads.

Figure 6:
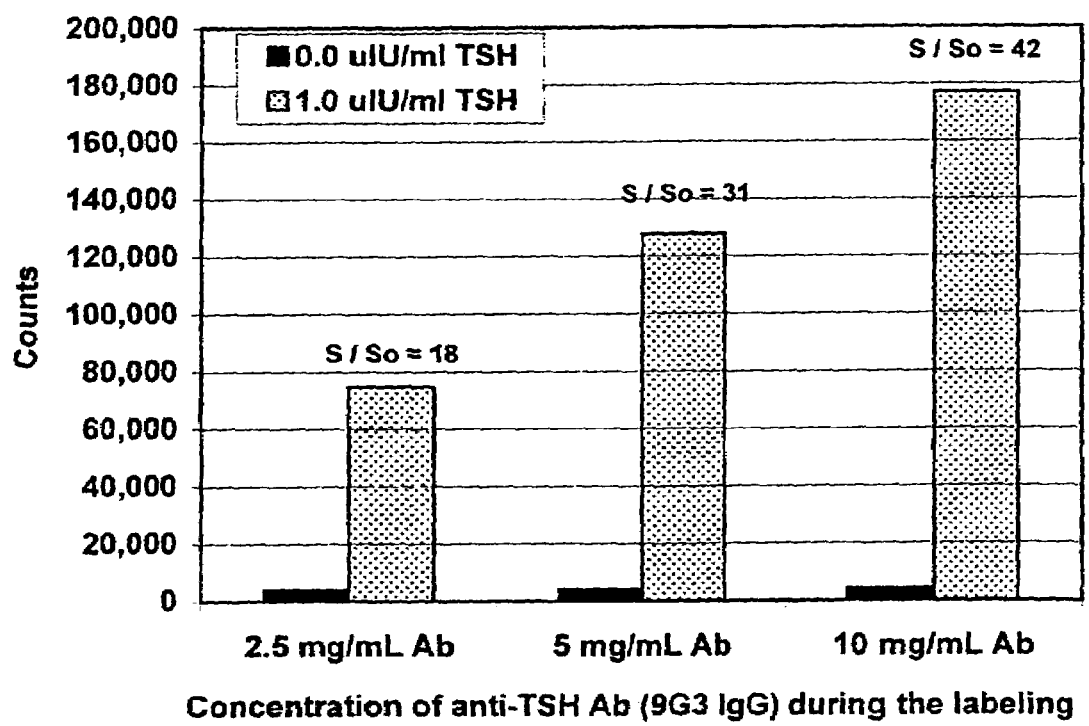

For preparation of anti-TSH labeled chemibead (C-bead-$Ab_2$) by double coating method, the effect of Ab concentration in the labeling reaction mixture was investigated. As shown in FIG. 6, the results showed that higher Ab concentration during the labeling resulted in chemibead-Ab reagent with better performance in the TSH LOCI™ assay. This TSH LOCI™ assay was performed by the following procedure: 50 µl TSH calibrators (0.0 or 1.0 µIU/ml TSH) in horse serum were reacted with 25 µl of R1 (Chemibead labeled with varying concentrations of anti-TSH $Ab_2$) and 25 µl of R2 (biotinylated anti-TSH $Ab_1$) for about 7.3 minutes at 37° C., then by reaction with 800 µlof R3 (streptavidin labeled sensitizer beads) for another 7.1 minutes at 37° C. and finally the LOCI™ signal was read.

A PSA (Prostate Specific Antigen) assay was performed to test the carboxy ethyl dextran coated beads. 40 µL buffer (0.1 M Tris/HCL pH 8.0, 0.3 M NaCl, 25 mM EDTA, 0.1% BSA, 0.1% Dextran T-500, 0.1% Triton X405), 25 µL anti-PSA conjugate (6.4 µg/mL antibody in 0.1 M Tris/HCL pH 8.0, 0.3 M NaCl, 25 mM EDTA, 1.6% BSA, 0.1% Dextran T-500, 0.1% Triton X-405, 0.2% B-IgG), 25 µL anti-PSA CEDex-beads (50 µg/mL in 0.1 M Tris/HCL pH 8.0, 0.3 M NaCl, 25 mM EDTA, 1.6% BSA, 0.1% Dextran T-500, 0.1% Triton X405, 0.2% B-IgG) and 10 µl serum sample are incubated. After an incubation time of 4.5 minutes buffer and 50 µL Sensitizer (400 µg/mL in 0.1 M Tris/HCL pH 8.0, 0.3 M NaCl, 25 mM EDTA, 0.1% BSA, 0.1% Dextran T-500, 0.1% Triton X405) are added

| PSA Assay Results | | | | | |
|---|---|---|---|---|---|
| Concentration | | | Signal | | |
| PSA [ng/mL] | Standard deviation | Coefficient of variation | Counts (n = 3) | Standard deviation | Coefficient of variation |
| 0.0 | | 11.8% | 3117.3 | 128 | 4.1% |
| 0.1 | 0.0 | 0.9% | 4782.3 | 9.5 | 0.2% |
| 1.3 | 0.01 | 0.7% | 18218 | 105 | 0.6% |
| 6.1 | 0.11 | 1.8% | 76778 | 1487 | 1.9% |
| 11.6 | 0.27 | 2.4% | 164711 | 3964 | 2.4% |
| 54.8 | 1.08 | 2.0% | 797016 | 15554 | 2.0% |
| 102.6 | 1.7 | 1.6% | 1436440 | 21361 | 1.5% |

39 mamma carcinoma sera have been tested in the PSA assay with DC-CEDex beads. These PSA negative serum samples are used as an indicator for potentially occuring matrix interferences. The results show that there are no matrix interferences disturbing the determination of PSA in serum samples. The coefficient of variation of these 39 serum samples is 5.1% with a standard deviation of 142 counts.

While the present invention has been described with reference to the specific embodiments thereof, it will be understood by and obvious to those skilled in the art that carious changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of claims appended hereto.

The invention claimed is:

1. A polysaccharide coated carrier comprising a carrier having a coating of at least two successive layers of polysaccharides, wherein a first polysaccharide layer is associated with a second polysaccharide layer and wherein the first polysaccharide is an aminodextran and the second polysaccharide is an amine-reactive dextran.

2. The carrier of claim 1 wherein each of said successive polysaccharide layers alternate between an aminodextran and an amine reactive dextran.

3. The carrier of claim 1 wherein said polysaccharides have pendent functional groups and said functional groups of said successive polysaccharide layers are charged oppositely of said functional groups of said preceding polysaccharide layers.

4. The carrier of claim 1 wherein said polysaccharides have pendant functional groups and said successive layers of polysaccharide are covalently coupled to said preceding polysaccharide layers by reaction between said functional groups of said successive layers with said functional groups of said preceding layers.

5. The carrier of claim 4 wherein the reaction between said functional groups is a spontaneous reaction.

6. The carrier according to claim 1 wherein the amine reactive functional group of the amine reactive dextran is an aldehyde group or a carboxyl group.

7. The carrier of claim 1 wherein said first polysaccharide layer is associated with said carrier through oppositely charged functional groups.

8. The carrier of claim 7 wherein said carrier and said polysaccharides have pendent functional groups.

9. The carrier of claim 8 wherein said carrier is a carboxylated carrier.

10. The carrier according to claim 1 wherein said carrier material is selected from the group consisting of natural, synthetic or modified naturally occurring polymers; silicones; glasses; ceramics; inorganic powders; magnetic materials; and metals; or a combination thereof.

11. The carrier according to claim 1 wherein said carrier is selected from the group consisting of strips, sheets, rods, tubes, wells, microtitration plates, beads and particles.

12. The carrier according to claim 1 wherein said carrier is a magnetic or non-magnetic particle.

13. The carrier according to claim 1 wherein said carrier is a carboxylated latex particle.

14. The carrier according to claim 13 wherein said particle is in the size range of 0.1 to 10 µm.

15. The carrier according to claim 1 of wherein said carrier is associated with at least one reporter molecule.

16. The carrier according to claim 15 wherein said reporter molecule is selected from the group consisting of dyes, radiolabels, sensitizers, fluorescers and chemiluminescers.

17. The carrier according to claim 1 wherein said aminodextran has a molecular weight of 10,000 to 2,000,000 daltons.

18. The carrier according to claim 1 wherein the outermost layer of polysaccharide has at least one pendent functional group.

19. The carrier according to claim 18 wherein said pendent functional group is selected from the group consisting of aldehydes, carboxyl groups, maleimido groups, and sulfhydryl groups.

20. The carrier according to claim 18 wherein said pendent functional group is bound to a specific binding partner.

21. The carrier according to claim 20 wherein said specific binding partner is selected from the group consisting of antibodies, antibody fragments, receptors, ligands, oligonucleotides, oligonucleotide-binding proteins, lectins, haptens, antigens, immunoglobulin binding proteins, avidin, streptavidin, and biotin.

22. A method for preparing the polysaccharide coated carrier of claim 1 wherein the carrier comprises amine reactive functional groups, said method comprising:
   (a) covalently coupling the first polysaccharide layer to said carrier by reaction between the amine reactive functional groups of the carrier and the amine functional groups of the polysaccharide of the first coating layer; and
   (b) covalently coupling the second polysaccharide layer to the first polysaccharide layer by reaction between the amine functional groups of the first polysaccharide layer and the amine reactive functional groups of the second polysaccharide layer.

23. The method according to claim 22 wherein carbodiimide conjugation chemistry is used for the coupling of the polysaccharides of the first coating layer to said carrier.

24. The method according to claim 22 wherein the coupling of the polysaccharides of the second coating layer to the first coating layer is done in the presence of a mild reducing agent.

25. The method according to claim 22 wherein carbodiimide conjugation chemistry is used for the coupling of the polysaccharides of the second coating layer to the first coating layer.

26. The method according to claim 22 wherein the specific binding partners are covalently bound to the coating layer by reaction between the pendent functional groups of the coating layer and functional groups of the specific binding partners.

27. The carrier according to claim 1 for use in in-vitro and/or in-vivo diagnostic methods.

28. The carrier according to claim 1 for use in a method for the quantitative and/or qualitative determination of an analyte.

29. Composition comprising the carrier according to claim 1 in a pharmaceutically acceptable medium.

30. The carrier according to claim 1 for use in a therapeutic method.

31. A method for quantitative or qualitative determination of an analyte in a sample, said method comprising:
   (a) combining in an assay medium a sample suspected of containing the analyte and a carrier according to claim 1 wherein the carrier comprises a specific binding partner for the analyte and
   (b) determining the extent of binding of the analyte to the specific binding partner for the analyte, the extent thereof being related to the presence or amount of the analyte in the sample.

32. A method for quantitative or qualitative determination of an analyte in a sample, said method comprising:
   (a) combining in an assay medium a sample suspected of containing the analyte and a carrier according to claim 1 wherein the carrier comprises an analyte analog and the medium further comprises a specific binding partner for the analyte and
   (b) determining the extent of binding of the analyte to the specific binding partner for the analyte, the extent thereof being related to the presence or amount of the analyte in the sample.

* * * * *